US007964564B2

(12) United States Patent
Burnett, Jr. et al.

(10) Patent No.: US 7,964,564 B2
(45) Date of Patent: *Jun. 21, 2011

(54) CHIMERIC NATRIURETIC PEPTIDES

(75) Inventors: John C. Burnett, Jr., Rochester, MN (US); Ondrej Lisy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 12/120,842

(22) Filed: May 15, 2008

(65) Prior Publication Data

US 2009/0170756 A1    Jul. 2, 2009

Related U.S. Application Data

(63) Continuation of application No. 10/947,730, filed on Sep. 23, 2004, now Pat. No. 7,384,917, which is a continuation of application No. 10/106,806, filed on Mar. 26, 2002, now Pat. No. 6,818,619, which is a continuation-in-part of application No. 09/466,268, filed on Dec. 17, 1999, now Pat. No. 6,407,211.

(51) Int. Cl.
*A61K 38/00* (2006.01)
(52) U.S. Cl. .................... 514/12; 514/2; 530/350; 435/6
(58) Field of Classification Search .................... None
See application file for complete search history.

(56) References Cited

U.S. PATENT DOCUMENTS

| 3,842,067 A | 10/1974 | Sarantakis |
| 3,862,925 A | 1/1975 | Sarantakis et al. |
| 3,972,859 A | 8/1976 | Fujino et al. |
| 4,051,842 A | 10/1977 | Hazel et al. |
| 4,105,602 A | 8/1978 | Colescott et al. |
| 4,140,122 A | 2/1979 | Kuhl et al. |
| 4,161,521 A | 7/1979 | Veber et al. |
| 4,383,529 A | 5/1983 | Webster |
| 4,683,195 A | 7/1987 | Mullis et al. |
| 4,757,048 A | 7/1988 | Lewicki et al. |
| 4,804,650 A | 2/1989 | Lewicki et al. |
| 4,935,492 A | 6/1990 | Lewicki et al. |
| 5,047,397 A | 9/1991 | Scarborough et al. |
| 5,114,923 A | 5/1992 | Seilhamer et al. |
| 5,202,239 A | 4/1993 | Tarnowski et al. |
| 5,322,930 A | 6/1994 | Tarnowski et al. |
| 5,560,922 A | 10/1996 | Chien et al. |
| 5,580,859 A | 12/1996 | Felgner et al. |
| 5,583,108 A | 12/1996 | Wei et al. |
| 5,674,710 A | 10/1997 | Seilhamer et al. |
| 5,691,310 A | 11/1997 | Vesely |
| 5,848,956 A | 12/1998 | Grettner |
| 5,948,761 A | 9/1999 | Seilhamer et al. |
| 6,124,430 A | 9/2000 | Mischak et al. |
| 6,162,902 A | 12/2000 | Mischak et al. |
| 6,407,211 B1 | 6/2002 | Burnett, Jr. et al. |
| 6,818,619 B2 | 11/2004 | Burnett, Jr. et al. |
| 7,384,917 B2 * | 6/2008 | Burnett et al. .................. 514/12 |

FOREIGN PATENT DOCUMENTS

| EP | 0 045 665 | 9/1985 |
| WO | WO 93/02556 | 2/1993 |
| WO | WO 99/12576 | 3/1999 |
| WO | WO 00/71576 | 11/2000 |

OTHER PUBLICATIONS

Abdallah et al., "Non-viral gene transfer: Applications in developmental biology and gene therapy," *Biol. Cell*, 1995, 85:1-7.
Adelman et al., "In Vitro Deletional Mutagenesis for Bacterial Production of the 20,000-Dalton Form of Human Pituitary Growth Hormone," *DNA*, 1983, 2(3):183-193.
Almquist et al., "Synthesis and Biological Activity of a Ketomethylene Analogue of a Tripeptide Inhibitor of Angiotensin Converting Enzyme," *J. Med. Chem.*, 1980, 23:1392-1398.
Atlas and Laragh, "Physiological Actions of Atrial Natriuretic Factor," *Atrial Hormones and Other Natriuretic Factors*, 1987, Mulrow et al. (eds.), Am. Physiol. Soc., Bethesda, MD, pp. 53-76.
Brenner et al., "Diverse Biological Actions of Atrial Natriuretic Peptide," *Physiol. Rev.*, 1990, 70:665-699.
Bruneau et al., "BNP gene expression is specifically modulated by stretch and ET-1 in a new model of isolated rat atria," *Am. J. Physiol.*, 1997, 273:H2678-H2686.
Burnett, Jr. et al., "Atrial Natriutetic Peptide Elevation in Congestive Heart Failure in the Human," *Science*, 1986, 231:1145-1147.
Burnett, Jr. et al., "Effects of synthetic atrial natriuretic factor on renal function and renin release," *Am. J. Physiol.: Renal Phy.*, 1984, 247(5 PT 2):F863-F866.
Carpino and Han, "The 9-Fluorenylmethoxycarbonyl Amino-Protecting Group," *J. Org. Chem.*, 1972, 37(22):3404-3409.
Cavero et al., "Cardiorenal Actions of Neutral Endopeptidase Inhibition in Experimental Congestive Heart Failure," *Circulation*, 1990, 82:196-201.
Clavell et al., "Biological actions of brain natriuretic peptide in thoracic inferior vena caval constriction," *Am. J. Physiol.*, 1993, 265:R1416-R1422.
Crea et al., "Chemical synthesis of genes for human insulin," *Proc. Natl. Acad. Sci. USA*, 1978, 75(12):5765-5769.

(Continued)

*Primary Examiner* — Hope A Robinson
(74) *Attorney, Agent, or Firm* — Fish & Richardson P.C.

(57) ABSTRACT

Peptides of *Dendroaspis*, including chimeric peptides thereof, are provided, as well as methods of using the peptides as natriuretics, diuretics, and/or vasodilators.

6 Claims, 15 Drawing Sheets

OTHER PUBLICATIONS

Barker and Dayhoff, "Detecting Distant Relationships: Computer Methods and Results," *Atlas of Protein Sequence and Structure*, 1972, vol. 5, National Biomedical Research Foundation, pp. 101-110.

de Bold et al., "A Rapid and Potent Natriuretic Response to Intravenous Injection of Atrial Myocardial Extract in Rats," *Life Sci.*, 1981, 28:89-94.

Donnelly et al., "Protective Efficacy of Intramuscular Immunization with Naked DNA," *Ann. N.Y. Acad. Sci.*, 1995, 772:40-46.

Edwards et al., "Atrial Stretch, Not Pressure, Is the Principal Determinant Controlling the Acute Release of Atrial Natriuretic Factor," *Circ. Res.*, 1988, 62:191-195.

Flynn et al., "The amino acid sequence of an atrial peptide with potent diuretic and natriuretic properties," *Biochem. Biophys. Res. Commun.*, 1983, 117(3):859-865.

Girbes et al., "Renal Function Is the Most Important Determinant of Survival in Patients With Severe Congestive Heart Failure," *J. Am. Coll. Cardiol.*, 1998, 31:154A.

Goeddel et al., "Synthesis of human fibroblast interferon by *E. coli*," *Nucl. Acids Res.*, 1980, 8(19):40157-4074.

Grantham and Burnett, Jr., "Natriuretic Peptides in Cardiovascular Disease," *Natriuretic Peptides in Health and Disease*, 1997, Samson and Levin (eds.), Humana Press, pp. 309-326.

Guo et al., "Protein tolerance to random amino acid change," *Proc. Natl. Acad. Sci. USA*, 2004, 101(25):9205-9210.

Cullen et al., "Crystal and Molecular Structure of a 4,5-Dimethyoxbilindione derived from Etiobiliverdin-IVγ: a Possible Model Compound for the Phytochrome Chromophore," *J. Chem. Soc. Perkin Trans.*, 1982, 1:307-312.

Holladay and Rich, "Synthesis of Hydroxyethylene and Ketomethylene Dipeptide Isosteres," *Tetrahedron Lett.*, 1983, 24(41):4401-4404.

Hruby, "Conformational Restrictions of Biologically Active Peptides Via Amino Acid Side Chain Groups," *Life Sci.*, 1982, 31:189-199.

Hudson et al., "Methionine Enkephalin 14:177-185 and Isosteric Analogues," *Int. J. Peptide Protein Res.*, 1979, 14:177-185.

Huntley et al., "BNP-Induced Activation of cGMP in Human Cardiac Fibroblasts: Interactions with Fibronectin and Natriuretic Peptide Receptors," *J. Cell. Physiol.*, 2006, 209:943-949.

Jennings-White and Almquist, "Synthesis of Ketomethylene Analogs of Dipeptides," *Tetrahedron Lett.*, 1982, 23:2533-2534.

Kambayashi et al., "Isolation and sequence determination of human brain natriuretic peptide in human atrium," *FEBS Lett.*, 1990, 259(2):341-345.

Koller et al., "Selective Activation of the B Natriuretic Peptide Receptor by C-Type Natriuretic Peptide (CNP)," *Science*, 1991, 252:120-123.

Lawn et al., "The sequence of human serum albumin cDNA and its expression in *E. coli*," *Nucl. Acids Res.*, 1981, 9(22):6103-6114.

Lebl and Hruby, "Synthesis of Cyclic Peptides by Solid Phase Methodology," *Tetrahedron Lett.*, 1984, 25(20):2067-2067.

Lin et al., "Human Atrial Natriuretic Peptide Gene Delivery Reduces Blood Pressure in Hypertensive Rats," *Hypertension*, 1995, 26:847-853.

Lisy et al., "A New Natriuretic Peptide Present in Canine Plasma and Heart," *J. Cardiac Failure*, 1998, 4(3), Suppl. 1, Abstract No. Y3, p. 1.

Lisy et al., "Renal actions of synthetic *Dendroaspis* natriuretic peptide," *Kidney International*, 1999, 56:502-508.

Lisy et al., "Therapeutic Action of a New Natriuretic and Vasoactive Peptide DNP in Experimental Severe Congestive Heart Failure," *Circulation*, 1999, 100(18) Supplement 1, Abstract No. 3354, pp. 1-636.

Lisy et al., "Therapeutic Actions of a New Synthetic Vasoactive and Natriuretic Peptide, Dendroaspis Natriuretic Peptide, in Experimental Severe Congestive Heart Failure," *Hypertension*, 2001, 37(4):1089-1094.

Lisy et al., "Unique Renal and Systemic Hemodynamic Actions of a New Natriuretic Peptide in Experimental Heart Failure," *JACC*, 1999, Abstract No. 1199-17, p. 202A.

McDonagh et al., "Biochemical detection of left-ventricular systolic dysfunction," *Lancet*, 1998, 351:9-13.

Meienhofer, "Peptide Synthesis: A Review of the Solid-Phase Method," *Hormonal Proteins and Peptides*, 1973, vol. 2, Li (ed.), Academic Press, pp. 45-267.

Chang and Meienhofer, "Solid-Phase Peptide Synthesis Using Mild Base Cleavage of Nα-Fluorenymethyloxycarbonylamino Acids, Exemplified by a Synthesisof Dihydrosomastatin," *Int. J. Peptide Protein Res.*, 1978, 11:246-249.

Merrifield, "Solid Phase Peptide Synthesis. I. The Synthesis of a Tetrapeptide," *J. Am. chem. Soc.*, 1963, 85:2149-2154.

Mölling, "Naked DNA for vaccine or therapy," *J. Mol. Med.*, 1997, 75:242-246.

Morley, "Modulation of the action of regulatory peptides by structural modification," *Trends Pharm. Sci.*, 1980, pp. 463-468.

Mukoyama et al., "Brain Natriuretic Peptide as a Novel Cardiac Hormone in Humans," *J. Clin. Invest.*, 1991, 87:1402-1412.

Mullis et al., "Specific Enzymatic Amplification of DNA in Vitro: The Polymerase Chain Reaction," *Cold Spring Harbor Symp. Quant. Biol.*, 1986, 51:263-273.

Needleman and Wunsch, "A General Method Applicable to the Search for Similarities in the Amino Acid Sequence of Two Proteins," *J. Mol. Biol.*, 1970, 48:443-453.

Nicholls, "The natriuretic peptides in heart failure," *J. Int. Med.*, 1994, 235:515-526.

Pardoll and Beckerleg, "Exposing the Immunology of Naked DNA Vaccines," *Immunity*, 1995, 3:165-169.

Pearson and Lipman, "Improved tools for biological sequence comparison," *Proc. Natl. Acad. Sci*, USA, 1988, 85:2444-2448.

Redfield et al., "Cardiorenal and Neurohumoral Function in a Canine Model of Early Left Ventricular Dysfunction," *Circulation*, 1993, 87:2016-2022.

Richards et al., "Atrial Natriuretic Hormone Has Biological Effects in Man at Physiological Plasma Concentrations," *J. Clin. Endo. Metab.*, 1988, 67(6):1134-1139.

Sambrook et al., *Molecular Cloning: A Laboratory Manual, 1989, Cold Spring Harbor Laboratory Press*, N.Y., Sections 4.21-4.41 and 9.47-9.51.

Scarborough et al., "Truncated Atrial Natriuretic Peptide Analogs," *J. Biol. Chem.*, 1986, 261(28):12960-12964.

Schiller et al., "A Novel Cyclic Opioid Peptide Analog Showing High Preference For μ-Receptors," *Biochem. Biophys. Res. Commun.*, 1985, 127:558-564.

Schiller et al., "Synthesis of side-chain to side-chain cyclized peptide analogs on solid supports," *Int. J. Peptide and Protein Res.*, 1985, 25:171-177.

Schirger et al., "Presence of *Dendroaspis* Natriuretic Peptide-Like Immunoreactivity in Human Plasma and Its Increase During Human Heart Failure," *Mayo Clin. Proc.*, 1999, 74:126-130.

Schweitz et al., "A New Member of the Natriuretic Peptide Family Is Present in the Venom of the Green Mamba (*Dendroaspis angusticeps*)," *J. Biol. Chem.*, 1992, 267(20):13928-13932.

Smith and Waterman, "Comparison of Biosequences," *Adv. Appl. Math.*, 1981, 2:482-489.

Spatola et al., "Structure-Activity of Enkephalins Containing Serially Replaced Thiomethylene Amide Bond Surrogates," *Life Sci.*, 1986, 38:1243-1249.

Spatola, "Peptide Backbone Modifications: A Structure-Activity Analysis of Peptides Containing Amide Bond Surrogates, Conformational Constraints and Rela . . . ," *Chemistry and Biochemistry of Amino Acids, Peptides, and Proteins*, 1983, vol. 7, Weinstein (ed)., Marcel Dekker, NY, Chapter 5, pp. 267-357.

Stein and Levin, "Natriuretic Peptides: Physiology, Therapeutic Potential, and Risk Stratification in Ischemic Heart Disease," *Am. Heart J.*, 1998, 135:914-923.

Steiner et al., "Radioimmunoassay for Cyclic Nucleotides," *J. Biol. Chem.*, 1972, 247(4):1106-1113.

Stevens et al., "A Functional Role for Endogenous Atrial Natriuretic Peptide in a Canine Model of Early Left Ventricular Dysfunction," *J. Clin. Invest.*, 1995, 95:1101-1108.

Stevens et al., "A Modified of Tachycardia-Induced Cardiomyopathy: Insights into Humoral and Renal Adaptations," *Pathophysiology of Tachycardia-Induced Heart Failure*, 1996, Futura Publishing Co., Inc. NY, pp. 133-151.

Stevenson et al., "Idiotypic DNA Vaccines Against B-cell Lymphoma," *Immunol. Rev.*, 1995, 145:211-228.

Stingo et al., "Cardiovascular and rental actions of C-type natriuretic peptide," *Am. J. Physiol.*, 1992, 262:H308-H312.

Stingo et al., "Presence of C-type natriuretic peptide in cultured human endothelial cells and plasma," *Am. J. Physiol.*, 1992, 263:H1318-H1321.

Sudoh et al., "C-Type Natriuretic Peptide (CNP): A New Member of Natriuretic Peptide Family Identified in Porcine Brain," *Biochem. Biophys. Res. Commun.*, 1990, 168(2):863-870.

Sudoh et al., "A new natriuretic peptide in porcine brain," *Nature*, 1988, 332:78-81.

Suga et al., "Endothelial Production of C-Type Natriuretic Peptide and Its Marked Augmentation by Transforming Growth Factor-β," *J. Clin. Invest.*, 1992, 90:1145-1149.

Tawaragi et al., "Gene and Precursor Structures of Human C-Type Natriuretic Peptide," *Biochem. Biophys. Res. Commun.*, 1991, 175(2):645-651.

Tripathy et al., "Immune responses to transgene-encoded proteins limit the stability of gene expression after injection of replication-defective adenovirus vectors," *Nature Med.*, 1996, 2:545-550.

Tripathy et al., "Stable delivery of physiologic levels of recombinant erythropoietin to the systemic circulation by intramuscular injection of replication-defective adenovirus," *Proc. Natl. Acad. Sci. USA*, 1994, 91:11557-11561.

Tripathy et al., "Long-term expression of erythropoietin in the systemic circulation of mice after intramuscular injection of a plasmid DNA vector," *Proc. Natl. Acad. Sci. USA*, 1996, 93:10876-10880.

Tsuruda et al., "Brain Natriuretic Peptide Is Produced in Cardiac Fibroblasts and Induces Matrix Metalloproteinases," *Circ. Res.*, 2002, 91:1127-1134.

Tsurumi et al., "Direct Intramuscular Gene Transfer of Naked DNA Encoding Vascular Endothelial Growth Factor Augments Collateral Development and Tissue Perfusion," *Circulation*, 1996, 94:3281-3290.

Vieira and Messing, "Production of Single-Stranded Plasmid DNA," *Meth. Enzymol.*, 1987, 153:3-11.

von Geldern et al., "Small Atrial Natriuretic Peptide Analogues: Design, Synthesis, and Structural Requirements for Guanylate Cyclase Activation," *J. Med. Chem.*, 1992, 35:808-816.

Wei et al., "Natriuretic Peptide System in Human Heart Failure," *Circulation*, 1993, 88:1004-1009.

Wells, "Additivity of Mutational Effects in Proteins," *Biochemistry*, 1990, 29(37):8509-8517.

Wennberg et al., "Inhibition of Nitric Oxide (NO), but not Neutral Endopeptidase (NEP), Augments CNP-mediated Coronary Relaxation in CHF," *Am. Coll. Cardiol.*, 1997, 29:305A.

Wolff et al., "Direct Gene Transfer into Mouse Muscle in Vivo," *Science*, 1990, 247:1465-1468.

Yamamoto et al., "Ventricular remodeling during development and recovery from modified tachycardia-induced cardiomyopathy model," *Am. J. Physiol.*, 1996, 271:R1529-R1532.

Yamamoto et al., "Effect of endogenous natriuretic peptide system on ventricular and coronary function in failing heart," *Am. J. Physiol.*, 1997, 273:H2406-H2414.

Yang et al., "Developing particle-mediated gene-transfer technology for research into gene therapy of cancer," *Mol. Med. Today*, 1996, 2:476-481.

\* cited by examiner

FIG. 4A

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 8

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

CHIMERIC NATRIURETIC PEPTIDES

CROSS-REFERENCE TO RELATED APPLICATIONS

This application is a continuation of U.S. application Ser. No. 10/947,730, filed Sep. 23, 2004, now U.S. Pat. No. 7,384,917, which is a continuation of U.S. application Ser. No. 10/106,806, filed Mar. 26, 2002, now U.S. Pat. No. 6,818,619, which is a continuation-in-part of U.S. application Ser. No. 09/466,268, filed Dec. 17, 1999, now U.S. Pat. No. 6,407,211, the disclosures of which are incorporated by reference herein.

STATEMENT OF GOVERNMENT SUPPORT

The invention was made with Government support under grant no. HL36634, awarded by the National Heart, Lung & Blood Institute. The Government has certain rights in the invention.

BACKGROUND OF THE INVENTION

Atrial natriuretic peptide (ANP) is the first described peptide in a family of hormones which regulate body fluid homeostasis (see Brenner et al., 1990). The description of the potent diuretic and natriuretic properties of atrial extracts by de Bold et al. (1981) was the first evidence that the heart could be an endocrine organ. The subsequent isolation and characterization of this activity by groups including Flynn et al. (1981) characterized ANP as the first secreted cardiac hormone. ANP is secreted by atrial myocytes in response to increased intravascular volume. Once it is in the circulation, its effects are primarily on the kidney, vascular tissue, and adrenal gland, in which its actions lead to the excretion of sodium and water by the kidneys and a decrease in intravascular volume and blood pressure (Atlas et al., 1987).

Matsuo and his coworkers isolated two other natriuretic peptides. Brain natriuretic peptide (BNP) and C-type natriuretic peptide (CNP) were both isolated from porcine brain extracts on the basis of their potent relaxant effects on chick rectum (Sudeh et al., 1988; Sudeh et al., 1990). BNP is of myocardial cell origin, and like ANP circulates in human plasma (de Bold et al., 1981; Burnett et al., 1984). BNP is natriuretic, renin inhibiting, vasodilating, and lusitropic (Mukoyama et al., 1991; Yamamoto et al. 1996; Grantham et al., 1996). CNP is of endothelial cell origin and functions as a vasodilating and growth-inhibiting peptide (Suga et al., 1992; Stingo et al., 1992; Koller et al., 1991). ANP and BNP are increased in the plasma and heart during congestive heart failure (CHF) in humans, and they exert important cardiorenal protective actions in addition to serving as serum markers for ventricular dysfunction (Stevens et al., 1995; Yamamoto et al., 1997; McDonagh et al., 1998).

ANP, BNP and CNP are synthesized from large precursor proteins, and the mature, active peptides have a 17 amino acid loop formed by an intramolecular disulfide linkage. In the human peptides, eleven of these amino acids are identical in ANP, BNP, and CNP, whereas the N- and C-terminal tails vary in both length and composition (see Kambayashi et al., 1990; and Tawaragi et al., 1991). CNP has no C-terminal tail, and studies of the structure of the gene for CNP demonstrated that translation is terminated by a stop codon immediately after the final cysteine codon in the mRNA.

Among species, the amino acid sequence of both ANP and CNP are highly conserved, whereas the structure of BNP varies greatly. For example, the mature 28 amino acid human and porcine ANPs are identical, and there is only one substitution in the rat peptide. The existence of this structural variation, coupled with the presence of at least three types of receptors specific for the natriuretic peptides, suggests that the physiological control of body fluid homeostasis is complex. ANP and CNP both decrease cardiac preload. However, unlike ANP, CNP is not natriuretic (Stingo et al., 1992).

The diverse actions of ANP, BNP and CNP on both the cardiovascular system and the kidney, as well as their roles in pathophysiological states such as heart failure, hypertension, and renal disease, have made the native peptides and their analog molecules of great interest to both clinical and basic scientists. See, for example, Lewicki et al. (U.S. Pat. Nos. 5,114,923, 4,804,650 and 4,757,048), Johnson et al. (U.S. Pat. No. 5,047,397) and Johnson et al. (U.S. Pat. No. 4,935,492), and Wei et al. (U.S. Pat. No. 5,583,108). U.S. Pat. No. 5,583,108 relates to a chimera of ANP and CNP, termed vasonatrin peptide (VNP). VNP, which includes 22 amino acids of CNP and the 5 amino acids at the carboxy-terminus of ANP, has arterial and venous vasodilating and natriuretic effects.

A fourth natriuretic peptide (NP), Dendroaspis natriuretic peptide (DNP), possesses structural similarity to ANP, BNP, and CNP. Isolated from the venom of Dendroaspis angusticeps or green mamba snake, DNP is a 38 amino acid peptide that contains a 17 amino acid disulfide ring structure similar to that of ANP, BNP, and CNP (FIG. 1), all of which mediate biologic actions through particulate guanylyl cyclase receptors and generation of cyclic guanosine monophosphate (cGMP) (Schweitz et al., 1992). DNP vasorelaxes rodent aorta and isolated canine coronary arteries with potency comparable to that of ANP (Schweitz et al., 1992; Wennberg et al., 1997). Additionally, DNP substantially augments the formation of cGMP, the second messenger for the other natriuretic peptides, in aortic endothelial cells (Schweitz et al., 1992).

Thus, there is a continuing need to identify peptides with properties such as those of natriuretic peptides which are useful to prevent or treat cardiovascular disorders, e.g., congestive heart failure.

SUMMARY OF THE INVENTION

The present invention provides an isolated and purified peptide compound having natriuretic, renin-suppressing, diuretic and/or vasodilator activity in mammals. Preferably, the peptide comprises a compound of formula (I):

(SEQ ID NO:4)
$X_0$-Pro-$X_1$-$A_5$-$A_1$-$A_3$-Pro-$A_1$-Pro-$A_1$-$A_5$-Pro-$X_1$-$X_1$-$X_1$-$A_4$ wherein $A_1$ is Leu, Lys, Arg, His, Orn, Asn or Gln; $A_3$ is Asp or Glu; $A_4$ is Lys, Arg, Orn, Ala, Thr, Asn, or Gln; $A_5$ is Gly, Ala, Val, Met, Leu, Norleucine or Ile; $X_0$ is absent or is a peptide of from 1 to 35 amino acid residues, preferably of from 1 to 25 amino acid residues, which peptide has a Cys residue at the C-terminus, and more preferably residues from the N-terminus of BNP or CNP; and $X_1$ is Ser or Thr; or a compound of formula (II):

(SEQ ID NO:12)
$X_0$-Pro-$X_1$-$A_5$-$A_1$-$A_3$-Pro-$A_1$-Pro-$A_1$-$A_5$-Pro-$X_1$-$X_1$-$X_1$-$A_4$-$X_2$ wherein $A_1$ is Leu, Lys, Arg, His, Orn, Asn or Gln; $A_3$ is Asp or Glu; $A_4$ is Lys, Arg, Orn, Ala, Thr, Asn, or Gln; $A_5$ is Gly, Ala, Val, Met, Leu, Norleucine or Ile; $X_2$ is absent or is a peptide of from 1 to 35 amino acid residues, preferably of from 1 to 25 amino acid residues; $X_0$ is absent or is a peptide of from 1 to 35 amino acid residues, preferably of from 1 to 25 amino acid residues, which peptide has a Cys residue at the C-terminus, and more preferably residues from the N-terminus of BNP or CNP; and $X_1$ is Ser or Thr.

One preferred peptide of the invention includes a chimeric peptide which is a 41 amino acid peptide combining the core ring structure of BNP with the C-terminus of DNP. Thus, a preferred compound of formula (I) is a chimeric peptide comprising Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Pro-Ser-Leu-Arg-Asp-Pro-Arg-Pro-Asn-Ala-Pro-Ser-Thr-Ser-Ala (SEQ ID NO:1; BD-NP; see FIG. 4), or a biologically active variant or fragment thereof. Preferably, the chimeric peptide has a disulfide bridge between Cys 10 and Cys 26. Other preferred peptides of the invention include a 37 amino acid peptide combining the core ring structure of CNP with the C-terminus of DNP. Thus, another preferred compound of formula (I) is a chimeric peptide comprising Gly-Leu-Ser-Lys-Gly-Cys-Phe-Gly-Leu-Lys-Leu-Asp-Arg-Ile-Gly-Ser-Met-Ser-Gly-Leu-Gly-Cys-Pro-Ser-Leu-Arg-Asp-Pro-Arg-Pro-Asn-Ala-Pro-Ser-Thr-Ser-Ala (SEQ ID NO:2; CD-NP; see FIG. 4), or a biologically active variant or fragment thereof. Preferably, the chimeric peptide has a disulfide bridge between Cys 6 and Cys 22. Thus, $X_0$, if present, is preferably the N-terminus of human BNP, i.e., Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys (SEQ ID NO:7), or the N-terminus of human CNP, i.e., Gly-Leu-Ser-Lys-Gly-Cys-Phe-Gly-Leu-Lys-Leu-Asp-Arg-Ile-Gly-Ser-Met-Ser-Gly-Leu-Gly-Cys (SEQ ID NO:8). Yet another preferred peptide includes a portion of the carboxy-terminus of DNP, preferably which includes the carboxy-terminal 15 amino acids (SEQ ID NO:3; see FIG. 4), or a biologically active variant or fragment thereof. As used herein, the term "biologically active" means that a peptide of the invention has at least one of the activities of a native natriuretic peptide. In one embodiment, the compound of formula (I) is a variant of SEQ ID NO:1, SEQ ID NO:2 or SEQ ID NO:3, i.e., the compound is not SEQ ID NO:1, SEQ ID NO:2 or SEQ ID NO:3.

Also provided is a compound which comprises a variant of a peptide fragment of *Dendroaspis* natriuretic peptide (SEQ ID NO:10), i.e., a variant of SEQ ID NO:3, wherein the variant has one or more amino acid substitutions selected from the group consisting of Gly to Pro; Glu to Asp; Val to Ile, Leu, Met, Phe, Ala or Nor; Met to Leu, Phe or Ile; Lys to Arg, Gln or Asn; Tyr to Trp, Phe, Thr or Ser; Asp to Glu; Phe to Leu, Val, He or Ala; His to Asn, Gln, Lys or Arg; He to Leu, Val, Met, Phe, Nor or Ala; Cys to Ser; Pro to Gly; Ser to Thr; Thr to Ser; Arg to Lys, Gln or Asn; Ala to Val, Ile, or Leu; Leu to Nor, Ile, Val, Met, Ala, or Phe; Asp to Glu; and Asn to Gln, His, Lys or Arg. In one embodiment, the compound comprises a variant of a peptide fragment of SEQ ID NO:3, wherein the variant has one or more amino acid substitutions selected from the group consisting of Pro to Gly; Ser to Thr; Thr to Ser; Arg to Lys; Gln or Asn; Ala to Val, Ile, or Leu; Leu to Nor, Ile, Val, Met, Ala, or Phe; Asp to Glu; and Asn to Gln, His, Lys or Arg. More preferably, the variant has one or more amino acid substitutions selected from the group consisting of Ser to Thr; Thr to Ser; Arg to Lys; Gln or Asn; Ala to Val, Ile, or Leu; Leu to Nor, Ile, Val, Met, Ala, or Phe; Asp to Glu; and Asn to Gln, His, Lys or Arg.

As described below, BD-NP has a combined effect in vivo, which includes potent vasodilatation with a focus on pulmonary vasodilation, natriuresis and suppression of renin. For example, in normal mammals, the administration of BD-NP significantly increases glomerular filtration rate (GFR), decreases proximal fractional reabsorption of sodium (PFRNa), and more strongly suppresses plasma renin activity, relative to the administration of DNP. Further, in normal mammals, the administration of BD-NP (e.g., at 50 ng/kg/minute) has no effect on renal blood flow (RBF), increases urinary cGMP excretion (UcGMPV), has a potent renin suppressing effect, more potently decreases mean arterial pressure (MAP), and more potently decreases right atrial pressure (RAP) and pulmonary capillary pressure (PCWP) with more potent pulmonary vasodilatation, relative to the administration of BNP.

As also described herein below, DNP-like immunoreactivity (DNP-LI) was present in human plasma and in the atrial myocardium, as well as in human urine. Moreover, DNP-LI was increased in human plasma in patients with CHF. DNP is also present in other mammalian species, e.g., in the canine plasma, urine and myocardium. In vivo, DNP is a very powerful stimulator of plasma and urinary cGMP generation and has potent natriuretic, diuretic, vasodilatory and renin-suppressing properties (Lisy et al., 1999b). Further, DNP shows therapeutic efficacy in normal canine (see Lisy et al., 1999b) as well as in a canine model of experimental heart failure (Lisy et al., 1999a).

As further described hereinbelow, the exogenous administration of DNP to dogs with mild or overt congestive heart failure resulted in decreases in cardiac filling pressures and mean arterial pressure, preserves cardiac output and increases glomerular filtration rate. Thus, the present invention provide a method to treat congestive heart failure which comprises the administration of DNP or a biologically active portion thereof, a peptide which is a chimeric natriuretic peptide of DNP, or a biologically active variant or fragment thereof.

Thus, the present invention also provides a composition useful as a natriuretic, renin-suppressor, diuretic and/or vasodilator. The composition comprises a therapeutically effective amount of at least one peptide of the invention in combination with a pharmaceutically acceptable carrier. Therefore, the invention further provides a method for inducing natriuresis, diuresis or vasodilation in a mammal, e.g., a human. The method comprises administering to the mammal a pharmaceutically effective amount of compound or composition of the invention. The present peptides may be useful, either singly or in combination, to treat (ameliorate or prevent) a number of pathological conditions, including congestive heart failure, acute or chronic kidney failure, hypertension, cirrhosis of the liver, nephrotic syndrome, and other edematous states.

BRIEF DESCRIPTION OF THE FIGURES

FIG. 8 shows codons for various amino acids.

FIG. 9 depicts exemplary and preferred amino acid substitutions.

DETAILED DESCRIPTION OF THE INVENTION

Definitions

Figure 1:
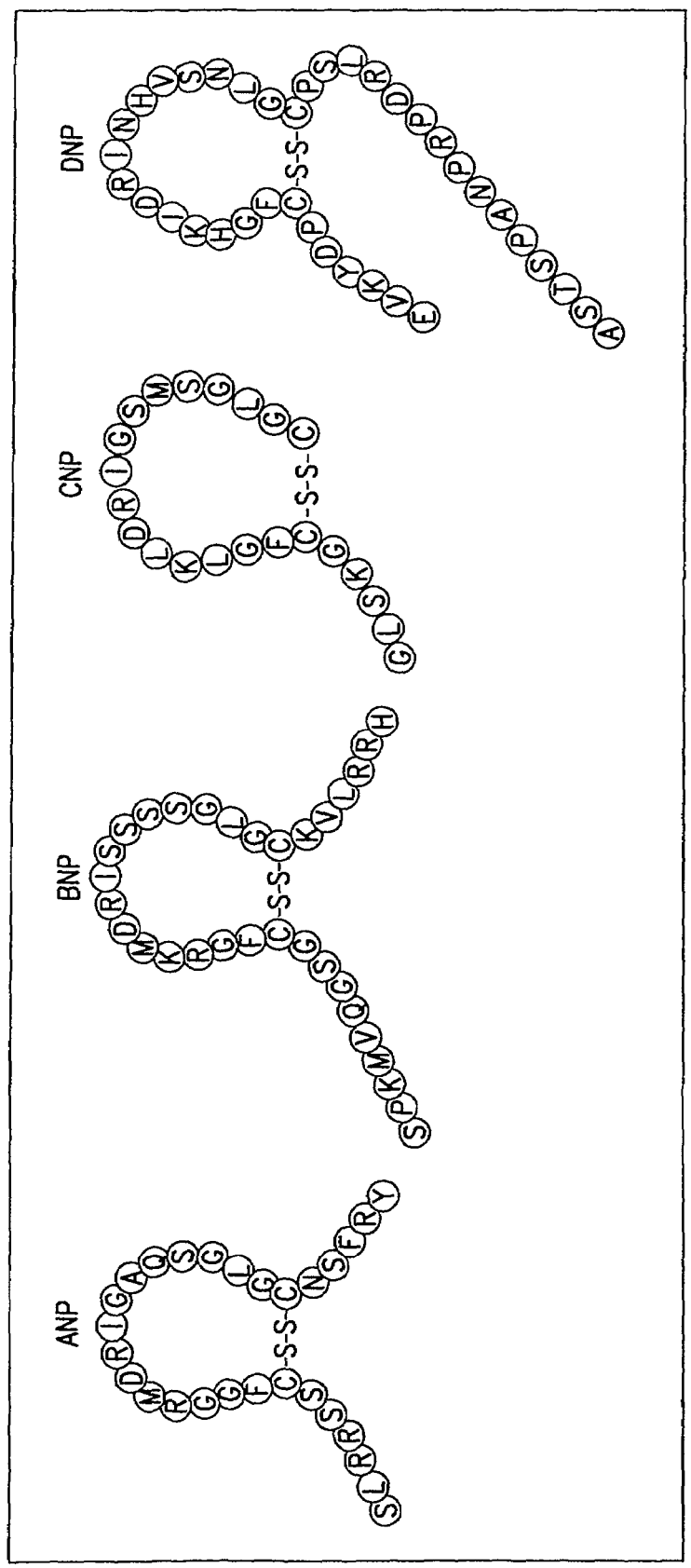
FIG. 1 shows the amino acid structures of atrial (ANP, 28 amino acids; SEQ ID NO:5), brain (BNP, 32 amino acids; SEQ ID NO:6), C-type (CNP, 22 amino acids; SEQ ID NO:9), and *Dendroaspis* (38 amino acids; SEQ ID NO: 10) natriuretic peptides.

As used herein, the term "natriuretic peptide" or "NP" includes a native NP, e.g., ANP, BNP, CNP or DNP, portions of a NP, variants of a NP, or chimeras thereof. Preferably, chimeras include only portions from the mature form of the NP.

As used herein, the terms "isolated and/or purified" refer to in vitro preparation, isolation and/or purification of a nucleic acid, e.g., DNA, or polypeptide molecule from its natural cellular environment, and from association with other components of the cell, such as nucleic acid or polypeptide, i.e., it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant nucleic acid sequence. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoranilate, phosphoroamidate, and the like. An oligonucleotide can include a label for detection, if desired.

For example, "isolated DNP nucleic acid" is RNA or DNA containing greater than 9, preferably 36, and more preferably 45 or more, sequential nucleotide bases that encode at least a portion of DNP or a RNA or DNA complementary thereto, that is complementary or hybridizes, respectively, to RNA or DNA encoding DNP and remains stably bound under stringent conditions, as defined by methods well known in the art, e.g., in Sambrook et al. (1989). Thus, the RNA or DNA is "isolated" in that it is free from at least one contaminating nucleic acid with which it is normally associated in the natural source of the RNA or DNA and is preferably substantially free of any other cellular, e.g., eukaryotic or mammalian, RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al. (1981), and Goeddel et al. (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

The term "isolated polypeptide or peptide" means a polypeptide or peptide, for example, encoded by DNA or RNA, including synthetic DNA or RNA, or some combination thereof, which isolated polypeptide or peptide (1) is not associated with proteins found in nature, (2) is free of other proteins from the same source, e.g., free of human proteins, (3) is expressed by a cell from a different species, or (4) does not occur in nature. An "isolated" peptide contains greater than 3, preferably greater than 6, and more preferably 12 or more amino acid residues.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Nucleic acid molecules falling within the scope of the invention include those which hybridize under stringent hybridization conditions to a nucleic acid molecule encoding a NP of the invention, e.g., nucleic acid molecules encoding SEQ ID NO:1, SEQ ID NO:2, or SEQ ID NO:3. Moderate and stringent hybridization conditions are well known to the art, see, for example, sections 9.47-9.51 of Sambrook et al. (1989). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium phosphate, 5× Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by visual and/or manual inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such-as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

I. Nucleic Acid Molecules of the Invention

A. Sources of the Nucleic Acid Molecules of the Invention

Sources of nucleotide sequences from which nucleic acid molecules encoding a NP of the invention, or the nucleic acid complement thereof, can be obtained include total or polyA$^+$ RNA from any eukaryotic, preferably reptilian, e.g., snake, or mammalian, e.g., human, rat, mouse, canine, bovine, equine, ovine, caprine, feline, more preferably primate, e.g., human, cellular source from which cDNAs can be derived by methods known in the art. Other sources of the DNA molecules of the invention include genomic libraries derived from any eukaryotic, preferably mammalian, cellular source, e.g., those exemplified above.

B. Isolation of a Gene Encoding NP

A nucleic acid molecule encoding a native NP can be identified and isolated using standard methods, as described by Sambrook et al. (1989). For example, reverse-transcriptase PCR (RT-PCR) can be employed to isolate and clone NP cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (a monophasic solution of phenol and guanidine isothiocyanate; GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., 1987; Erlich, 1989. Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic NPs. One primer is prepared which is predicted to anneal to the antisense strand, and another primer prepared which is predicted to anneal to the sense strand, of a DNA molecule which encodes, for example, a human DNP-like immunoreactive polypeptide (e.g., DNP-LI).

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode a NP is to screen a cDNA library. Screening for DNA fragments that encode all or a portion of a cDNA encoding a NP can be accomplished by probing the library with a probe which has sequences that are highly conserved between genes believed to be related to the NP, e.g., the homolog of a particular NP from a different species, or by screening of plaques for binding to antibodies that specifically recognize a NP. DNA fragments that bind to a probe having sequences which are related to NP, or which are immunoreactive with antibodies to NP, can be subcloned into a suitable vector and sequenced and/or used as probes to identify other cDNAs encoding all or a portion of the NP.

C. Variant or Chimeric NP Encoded by the Nucleic Acid Molecules of the Invention Nucleic acid molecules encoding amino acid sequence variants of a native NP are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the NP, or by chemical syntheses (see below). Chimeric NPs may be prepared, for example, by using recombinant DNA based methodologies or chemical syntheses. For example, a chimeric NP may be prepared using overlapping oligonucleotides and PCR. A sense oligonucleotide encoding at least a portion of the amino-terminal residues of one NP and a portion of a second NP is annealed to an antisense oligonucleotide that has sequences complementary to the sequences at the 3' of the sense oligonucleotide as well as other sequences complementary to those encoding the carboxy-terminus of the chimeric NP. PCR is then employed to prepare a double-stranded DNA encoding the full length chimeric NP.

For amino acid substitution variants of a NP, a preferred method for preparing the variants is oligonucleotide-mediated mutagenesis. This technique is well known in the art as described by Adelman et al. (1983). Briefly, for example, DNP DNA is altered by hybridizing an oligonucleotide encoding the desired mutation to a DNA template, where the template is the single-stranded form of a plasmid or bacteriophage containing the unaltered or native DNA sequence of the DNP. After hybridization, a DNA polymerase is used to synthesize an entire second complementary strand of the template that will thus incorporate the oligonucleotide primer, and will code for the selected alteration in the DNP DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. (1987). Thus, the DNA that is to be mutated may be inserted into one of these vectors to generate single-stranded template. Production of the single-stranded template is described in Sections 4.21-4.41 of Sambrook et al. (1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of, for example, DNP, and the other strand (the original template) encodes the native, unaltered sequence of DNP. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

For example, one embodiment of the invention is an isolated and purified DNA molecule comprising a DNA segment encoding the carboxy-terminal 15 amino acids of DNP (SEQ ID NO:3), which amino acids may be encoded by any codon that encodes that amino acid (see FIG. 8 and page D1 in Appendix D in Sambrook et al. (1989)).

It is also envisioned that one or more of the residues of the peptide encoded by the nucleic acid molecules of the invention can be altered, so long as the peptide variant has biological activity. It is preferred that the variant has at least about 10% of the biological activity of a peptide of the invention, e.g., a peptide having SEQ ID NO: 1, SEQ ID NO:2 or SEQ ID NO:3. The biological activity of a peptide of the invention may be determined using methods well known to the art, including immunoassays and in vivo studies, such as those described herein below.

II. Preparation of Agents Falling within the Scope of the Invention

A. Chimeric Expression Cassettes

To prepare expression cassettes for transformation, the recombinant or preselected DNA sequence or segment may be circular or linear, double-stranded or single-stranded. A preselected DNA sequence which encodes an RNA sequence that is substantially complementary to a mRNA sequence encoding a NP, such as a DNA encoding a chimeric NP comprising BNP and DNP, is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein with respect to a cassette or vector, "chimeric" means that a vector comprises DNA from at least two different species, or comprises DNA from the same species, which is linked or associated in a manner which does not occur in the "native" or wild type of the species.

Aside from preselected DNA sequences that serve as transcription units for NP, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (1989) provides suitable methods of construction.

B. Transformation into Host Cells

The recombinant DNA can be readily introduced into the host cells, e.g., mammalian, bacterial, yeast or insect cells, by transfection with an expression vector comprising DNA encoding a NP, a variant thereof, a chimera thereof, or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, viral vectors have become the most widely used method for introducing genes into mammalian, e.g., human, cells. Viral vectors can be derived from poxviruses, herpes simplex virus I, adenoviruses and adeno-associated viruses, retroviruses, lentiviruses and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding NP or its complement, which host cell may or may not express significant levels of autologous or "native" NP.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular NP, e.g., by immunological means (immunoassays, such as ELISA and Western blot) or by assays described herein to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host or host cell.

III. Peptides of the Invention

Peptides of this invention can be synthesized by the solid phase peptide synthesis (or Merrifield) method. This established and widely used method, including the experimental procedures, is described in the following references: Stewart et al., 1969; Merrifield, 1963; Meienhofer, 1973; and Barany and Merrifield, 1980. The synthesis is commenced from the carboxy-terminal end of the peptide using an alpha amino protected amino acid. Fluorenylmethyloxy-carbonyl (Fmoc) or t-butyloxycarbonyl (Boc) protective groups can be used for all amino groups even though other protective groups are suitable. For example, Boc-Asn-OH, Boc-Ser-OH, Boc-Phe-OH, Boc-Arg-OH or Boc-Tyr-OH (i.e., selected ANP analog carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be insoluble in certain organic solvents. See Carpino et al., 1972; Meinhofer, 1978; and Merrifield, 1963. These and other methods of peptide synthesis are also exemplified by U.S. Pat. Nos. 3,862,925; 3,842,067; 3,972,859, 4,105,602 and U.S. Pat. No. 4,757,048.

The immobilized peptide is then N-deprotected and other amino acids having protected amino groups are added in a stepwise manner to the immobilized peptide. At the end of the procedure, the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptides are isolated and purified by means well known in the art such as, for example, lyophilization followed by either exclusion or partition chromatography on polysaccharide gel media such as SEPHADEX™ G-25(a beaded gel filtration medium prepared by cross-linking dextran with epichlorohydrin under alkaline conditions), or countercurrent distribution. The composition of the final peptide may be confirmed by amino acid analysis after degradation of the peptide by standard means.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus, the C-terminal end of the peptide when freed from the resin is directly esterifies without isolation of the free acid.

Amides of the polypeptides of the present invention may also be prepared by techniques well known in the at for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared for example, by acylation of a free hydroxy peptide or peptide resin. Either acylation may be carried out using standard acylating reagent such as acyl halides, anhydrides, acyl imidazoles, and the like. Both—and O-acylation may be carried out together, if desired.

The synthesis may use manual techniques or be completely automated, employing, for example, an Applied BioSystems 431A Peptide Synthesizer (Foster City, Calif.) or a Biosearch SAM II automatic peptide synthesizer (Biosearch, Inc., San Rafael, Calif.), following the instructions provided in the instruction manual and reagents supplied by the manufacturer. Disulfide bonds between Cys residues can be introduced by mild oxidation of the linear peptide by KCN as taught in U.S. Pat. No. 4,757,048 at Col. 20.

Variant peptides of the invention, e.g., those having one or more amino acid substitutions relative to a native NP, may be prepared and modified as described above. Preferred variant peptides are those having conservative amino acid substitutions. Conservative amino acid substitutions are, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide can readily be determined by assaying the specific activity of the peptide variant. Conservative substitutions are shown in FIG. 9 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions peptide variants with non-conservative substitutions. Non-conservative substitutions entail exchanging a member of one of the classes described above for another. Such production can be desirable to provide large quantities or alternative embodiments of such compounds.

The cyclic compounds of the present invention can be provided by bonding cysteine residues, however, the replacement of a sulfhydryl group on the cysteine residue with an alternative group is also envisioned, for example, —$CH_2$—$CH_2$—. For example, to replace on sulfhydryl groups with a —$CH_2$— group, the cysteine residues are replaced by the analogous alpha-aminobutyric acid. These cyclic analog peptides can be formed, for example, in accordance with the methodology of M. Lebl and Hruby (1984), or by employing the procedure disclosed in U.S. Pat. No. 4,161,521.

Ester or amide bridges may also be formed by reacting the OH or serine or threonine and the carboxyl of aspartic acid or glutamic acid, to yield a bridge of the structure —$CH_2$—$CO_2CH_2$—. Similarly, an amide can be obtained by reacting the side-chain of lysine and aspartic or glutamic acid to yield a bridge of the structure —$CH_2$—$C(O)NH$—$(CH_2)_4$—. Methods for synthesis of these bridges are found in Schiller et al. (1985a) and Schiller et al. (1985b). Other bridge-forming amino acid residues and reactions are provided in U.S. Pat. No. 4,935,492.

The following references describe preparation of peptide analogs which include non-peptidyl bonds to link amino acid residues. Spatola, 1983a; Spatola, 1983b; Morley, 1980; Hudson et al., 1979; Spatola et al., 1986; Hann, 1982; Almquist et al., 1980; Jennings-White et al., 1982; Szelke et al., European patent application EP 45665 (1982); Holladay et al., 1983; and Hruby, 1982.

IV. Dosages, Formulations and Routes of Administration of the Agents of the Invention The nucleic acid molecules and peptides of the invention are preferably administered to a mammal, e.g., a human or a non-human mammal, such as a domestic animal, at dosages of at least about 0.01 to about 100 mg/kg, more preferably about 0.05 to about 50 mg/kg, and even more preferably about 0.1 to about 30 mg/kg, of body weight (e.g., about 10 to about 50 ng/kg in dogs), although other dosages may provide beneficial results. The amount administered will vary depending on various factors including, but not limited to, the agent chosen, the disease, and whether prevention or treatment is to be achieved. Both local and systemic administration are envisioned. Systemic administration is preferred.

Thus, administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., 1995; Stevenson et al., 1995; Molling, 1997; Donnelly et al., 1995; Yang et al., 1996; Abdallah et al., 1995; Wolff et al., 1990; Tripathy et al., 1994; Tripathy et al., 1996a; Tripathy et al., 1996b; Tsurumi et al., 1996; Baumgartner et al., 1997; Lin et al., 1990). Pharmaceutical formulations, dosages and routes of administration for nucleic acids are generally disclosed, for example, in Felgner et al., supra.

The peptide compounds may be formulated into the compositions as neutral or salt forms. Pharmaceutically acceptable nontoxic salts include the acid addition salts (formed with the free amino groups) and which are formed by reaction with inorganic acids such as, for example, hydrochloric, sulfuric or phosphoric acids, or organic acids such as, for example, acetic, oxalic, tartaric, mandelic, citric, malic, and the like. Salts formed with the free carboxyl groups may be derived from inorganic bases such as, for example, sodium, potassium, ammonium, calcium, or ferric hydroxides, and such organic bases such as amines, i.e., isopropylamine, trimethylamine, 2-ethylamino ethanol, histidine, procaine, and the like.

One or more suitable unit dosage forms comprising the nucleic acid molecule or peptide of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intracoronary, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the nucleic acid molecule or peptide of the invention is prepared for oral administration, it is preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the nucleic acid molecule or peptide of the invention can be prepared by procedures known in the art using well known and readily available ingredients. For example, the nucleic acid molecule or peptide can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the nucleic acid molecule or peptide of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing the nucleic acid molecule or peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of the nucleic acid molecule or peptide of the invention are designed to resist disintegration in the stomach and dissolve in the more neutral to alkaline environment of the duodenum.

The nucleic acid molecule or peptide of the invention can also be formulated as elixirs or solutions for convenient oral administration or as solutions appropriate for parenteral administration, for instance by intramuscular, subcutaneous or intravenous routes.

The pharmaceutical formulations of the nucleic acid molecule or peptide of the invention can also take the form of an aqueous or anhydrous solution or dispersion, or alternatively the form of an emulsion or suspension.

Thus, the nucleic acid molecule or peptide may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The nucleic acid molecule or peptide of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenevinyl alcohol copolymers, ethylenevinyloxyethanol copolymers;

silicone copolymers, for example, polysiloxanepolycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the nucleic acid molecule or peptide of the invention is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the nucleic acid molecule or peptide may be administered via nose drops, a liquid spray, such as via a plastic bottle atomizer or metered-dose inhaler. Typical of atomizers are the Mistometer (Wintrop) and the Medihaler (Riker).

The local delivery of the nucleic acid molecule or peptide of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the nucleic acid molecule or peptide may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of the nucleic acid molecule or peptide of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The nucleic acid molecule or peptide may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other therapeutic agents.

The invention will be further described by the following examples.

EXAMPLE 1

Materials and Methods

VNP was synthesized in the Mayo Protein Core Facility using fluorenylmethoxy-carbonyl (FMOC) chemistry on an ABI 431A peptide synthesizer (Applied Biosystems Inc., Foster City, Calif.) with the protocols and reagents supplied by the manufacturer. The peptide was purified by reverse phase high performance liquid chromatography (HPLC) using a Vydac C8 column (The Separations Group, Hesperia, Calif.). The synthesis was confirmed by amino acid analysis and plasma absorption mass spectrometry.

The samples from the plasma and urine were analyzed using reverse phase HPLC with a Vydac C18 column (4.6 mm.times.250 mm) (The Separations Group, Hesperia, Calif.). The components of the HPLC system were two Beckman 114 pumps (Beckman Instruments, San Ramon, Calif.), ABI 759A absorbance detector (Applied Biosystems, Inc., Foster City, Calif.), and an IBM PS2 50Z computer with Beckman SYSTEM GOLD® Chromatography software. The A buffer was 0.1% trifluoroacetic acid and the B buffer was 80% acetonitrile/20% water/0.1% trifluoroacetic acid. The separation was performed with a gradient of 5% to 70% B buffer in 60 minutes.

The results obtained are expressed as the means±SEM. In organ chamber studies, n equals the number of dogs from which rings were taken. Rings with and without endothelium were studied in parallel, and Student's t-test for unpaired observations was used to determine statistical significance among the responses of rings with and without endothelium and between responses of arteries and veins. In rat studies, the data were analyzed using ANOVA for repeated measures followed by Fisher's least significant difference test when appropriate within the group. Data between groups were analyzed by Student's unpaired t-test. Statistical significance was determined at p<0.05.

Experiments were conducted in accordance with the Animal Welfare Act. Wistar rats and spontaneously hypertensive rats (SHR) (400g; Harlan Sprague-Dawley, Indianapolis, In.) were anesthetized with Inactin (100 mg/kg; intraperitoneal; BYK Gulden, Konstanz, Germany). The body temperature was maintained between 36° and 38° C. by a heating pad. Tracheostomy was performed; however, the animals were not artificially ventilated. Polyethylene catheters (PE-50; Becton Dickinson Co., Parsippany, N.J.) were placed in the left jugular vein for infusions of saline and drugs, in the right jugular vein to right atrium to monitor right atrial pressure, and in the carotid artery for the collection of blood samples and to monitor mean arterial pressure. A PE-90 catheter was placed in the bladder for urine collection.

Experiments were conducted in three groups in normal rats: ANP group (n=4), CNP group (n=4), and VNP group (n=4). VNP also was studied in SHR rats (n=4). Intravenous infusions of saline solution (0.9% NaCl) were performed (1 ml/100 gm body weight/hour) through the left jugular vein catheter. After completion of surgery, rats were allowed to stabilize for 30 minutes. In each group, a 15 minute baseline period followed. After the baseline period, saline solution (0.9% NaCl) was administered in a bolus fashion (0.1 ml) and was followed by a 15 minute period. After the saline period, the peptide (ANP, CNP or VNP) was administered in a bolus fashion (0.1 ml) at 5 μg/kg which was followed by a 15 minute period. This was followed by a second bolus (0.1 ml) at 50 μg/kg and a 15 minute period. After a 30 minute washout, a 15 minute recovery period followed. During each experimental period, mean arterial pressure (MAP), heart rate (HR), and right atrial pressure (RAP) were measured. At the midpoint of baseline, second bolus fashion (50 μg/kg) and recovery periods, blood was sampled for plasma cGMP. At the end of each period, urine was measured for volume (UV), and samples were stored for electrolytes and cGMP analysis.

Blood for plasma cGMP analysis was collected into EDTA tubes, immediately placed on ice, and centrifuged at 2,5000 rpm at 4° C. Plasma was separated and stored at −20° C. until assay. Urine for cGMP determination was heated to >90° C. before storage. Plasma and urine cGMP were determined by a specific RIA as previously described by A. L. Steiner et al., *J. Hypertension,* 5 (Suppl. 5), 551-553 (1987).

Table 2 summarizes the cardiovascular and renal actions of ANP, CNP and VNP administration in normal rats.

As demonstrated by the data in Table 2, bolus administration (0.1 ml) of saline solution had no cardiovascular or renal actions. Bolus administration (0.1 ml) of high dose (50 μg/kg) ANP, CNP and VNP resulted in a significant decrease in MAP and RAP, and increased urine flow, sodium excretion, plasma cGMP and urinary cGMP volume. The increase in urine flow, sodium excretion and urinary cGMP volume were significantly higher with VNP than those of CNP, but were less than those of ANP.

Table 3 reports the cardiovascular and renal effects of VNP in normal and SHR rats.

TABLE 2

The cardiorenal actions of ANP, CNP and VNP in normal rats

| | | Baseline | Saline | 5 μg/kg | 50 μg/kg | Recovery |
|---|---|---|---|---|---|---|
| ANP group (n = 4) | | | | | | |
| MAP | (mmHg) | 119 ± 14 | 120 ± 14 | 97 ± 12* | 69 ± 7*+ | 92 ± 11*¶ |
| HR | (beats/minute) | 375 ± 23 | 365 ± 17 | 353 ± 14 | 355 ± 19 | 368 ± 23 |
| RAP | (mmHg) | 0.8 ± 1.6 | 0.5 ± 1.8 | −2.3 ± 0.8* | −3.8 ± 0.8*+ | −0.8 ± 0.9¶ |
| UV | (μl/minute) | 6.7 ± 1.2 | 7.2 ± 1.8 | 79 ± 10* | 341 ± 41*+ | 48 ± 14¶ |
| UNaV | (μmol/minute) | 0.4 ± 0.1 | 0.4 ± 0.1 | 13.2 ± 3.5* | 68.2 ± 15.7*+ | 8.9 ± 3.5¶ |
| UKV | (μmol/minute) | 1.8 ± 0.1 | 0.7 ± 0.1 | 10.3 ± 3.5 | 24.4 ± 8.7 | 2.4 ± 0.1 |
| PcGMP | (pmol/ml) | 4.1 ± 0.7 | 12 ± 2 | — | 25.7 − 7.1* | 3.2 − 63¶ |
| UcGMPV | (pmol/minute) | 11 ± 2 | 12 ± 2 | 605 ± 151* | 2580 ± 505*+ | 105 ± 63¶ |
| CNP group (n = 4) | | | | | | |
| MAP | (mmHg) | 116 ± 11 | 115 ± 12 | 100 ± 12* | 87 ± 9*+ | 104 ± 11*¶ |
| HR | (beats/minute) | 350 ± 9 | 360 ± 14 | 363 ± 19 | 365 ± 19 | 363 ± 16 |
| RAP | (mmHg) | 1.2 ± 0.9 | 0.2 ± 1.4 | 0 ± 1.5 | −2.3 ± 0.6* | −0.1 ± 0.9* |
| UV | (μl/minute) | 5.7 ± 0.5 | 5.7 ± 0.6 | 27.6 ± 2.0*§ | 66.4 ± 7.4*+§ | 21.2 ± 6.3¶ |
| UNaV | (μmol/minute) | 0.6 ± 0.2 | 0.6 ± 0.2 | 4.1 ± 1.4§ | 12.1 ± 3.2*+§ | 2.9 ± 0.3 |
| UKV | (μmol/minute) | 1.2 ± 0.3 | 1.2 ± 0.3 | 5.1 ± 1.6 | 7.6 ± 2.5 | 2.4 ± 1.1 |
| PcGMP | (pmol/ml) | 2.2 ± 0.1 | — | — | 19.4 ± 2.7* | 3.6 ± 0.3¶ |
| UcGMPV | (pmol/minute) | 23 ± 7 | 22 ± 6 | 97 ± 32§ | 323 ± 81*§ | 70 ± 39¶ |
| VNP group (n = 4) | | | | | | |
| MAP | (mmHg) | 112 ± 14 | 109 ± 12 | 93 ± 15* | 79 ± 15*+ | 93 ± 15*¶ |
| HR | (beats/minute) | 390 ± 24 | 398 ± 22 | 393 ± 20 | 408 ± 25 | 390 ± 20 |
| RAP | (mmHg) | −2.5 ± 0.6 | −2.1 ± 0.7 | −3.5 ± 0.9 | −4.3 ± 0.8* | −2.9 ± 0.9¶ |
| UV | (μl/minute) | 6.5 ± 1.1 | 6.4 ± 0.3 | 32.2 ± 7.5*§ | 136 ± 5.5*+§# | 8.4 ± 2.7¶ |
| UNaV | (μmol/minute) | 0.9 ± 0.3 | 0.7 ± 0.2 | 5.3 ± 1.9 | 22.5 ± 2.2*+§# | 0.9 ± 0.3¶ |

TABLE 2-continued

The cardiorenal actions of ANP, CNP and VNP in normal rats

| | | Baseline | Saline | 5 μg/kg | 50 μg/kg | Recovery |
|---|---|---|---|---|---|---|
| UKV | (μmol/minute) | 0.9 ± 0.1 | 1.0 ± 0.2 | 3.3 ± 1.4 | 11.9 ± 4.7 | 1.3 ± 0.6 |
| PcGMP | (pmol/ml) | 3.7 ± 1.2 | — | — | 33.3 ± 8.7* | 4.4 ± 1.4¶ |
| UcGMPV | (pmol/ml) | 13 ± 7 | 12 ± 6 | 113 ± 27*§ | 961 ± 82*+§# | 88 ± 48¶ |

Mean ± SEM
*$p < .05$ vs Baseline
+$p < .05$ vs 5 μg/kg
¶$p < .05$ vs 50 μg/kg
§$p < .05$ vs ANP group
$p < .05$ vs CNP group
ANP atrial natriuretic peptide
CNP C-type natriuretic peptide
VNP vasonatrin peptide
MAP mean arterial pressure
HR heart rate
RAP right atrial pressure
UV urine volume
UNaV urine sodium excretion
UKV urine potassium excretion
PcGMP plasma cGMP
UcGMPV urine cGMP volume

TABLE 3

The cardiorenal actions of VNP in normal and SHR rats

| | | Baseline | Saline | 5 μg/kg | 50 μg/kg | Recovery |
|---|---|---|---|---|---|---|
| | | Normal group (n = 4) | | | | |
| MAP | (mmHg) | 112 ± 14 | 109 ± 12 | 93 ± 15* | 79 ± 15*+ | 93 ± 15*¶ |
| HR | (beats/minute) | 390 ± 24 | 398 ± 22 | 393 ± 20 | 408 ± 25 | 390 ± 20 |
| RAP | (mmHg) | −2.5 ± 0.6 | −2.1 ± 0.7 | −3.5 ± 0.9 | −4.3 ± 0.8* | −2.9 ± 0.9¶ |
| UV | (μl/minute) | 6.5 ± 1.1 | 6.4 ± 0.3 | 32.2 ± 7.5* | 136 ± 5.5*+ | 8.4 ± 2.7¶ |
| UNaV | (μmol/minute) | 0.9 ± 0.1 | 1.0 ± 0.2 | 5.3 ± 1.9 | 22.5 ± 2.2*+ | 0.9 ± 0.2¶ |
| UKV | (μmol/minute) | 0.9 ± 0.1 | 1.0 ± 0.2 | 3.3 ± 1.4 | 11.9 ± 4.7 | 1.3 ± 0.6 |
| PcGMP | (pmol/ml) | 3.7 ± 1.2 | — | — | 33.3 ± 8.7* | 4.4 ± 1.4¶ |
| UcGMPV | (pmol/minute) | 13 ± 7 | 12 ± 6 | 113 ± 27* | 961 ± 82*+ | 88 ± 45¶ |
| | | SHR rats (n = 4) | | | | |
| MAP | (mmHg) | 169 ± 17§ | 168 ± 17§ | 132 ± 23* | 119 ± 20*+ | 138 ± 19*¶ |
| HR | (beats/minute) | 388 ± 13 | 390 ± 11 | 393 ± 13 | 405 ± 10 | 405 ± 17 |
| RAP | (mmHg) | 0.5 ± 1.2 | 0.5 ± 1.3 | −1.1 ± 0.8 | −2.5 ± 0.6*+ | −0.9 ± 1.0¶ |
| UV | (μl/minute) | 3.7 ± 1.3 | 3.8 ± 0.7§ | 26.8 ± 3.5* | 48.2 ± 7.4*+§ | 9.1 ± 3.7¶ |
| UNaV | (μmol/minute) | 0.5 ± 0.2 | 0.6 ± 0.2 | 5.2 ± 1.6* | 9.2 ± 2.1*+§ | 1.7 § 0.7¶ |
| UKV | (μmol/minute) | 0.6 ± 0.2 | 0.6 ± 0.2 | 3.9 ± 1.5 | 6.6 ± 2.6 | 1.1 ± 0.4 |
| PcGMP | (pmol/ml) | 3.1 ± 0.7 | — | — | 17.7 ± 3.6* | 3.1 ± 0.5¶ |
| UcGMPV | (pmol/minute) | 9 ± 1 | 8 ± 2 | 115 ± 27* | 234 ± 42*+§ | 26 ± 12¶ |

Mean ± SEM
*$p < .05$ vs Baseline
+$p < .05$ vs 5 μg/kg
¶$p < .05$ vs 50 μg/kg
§$p < .05$ vs ANP group
$p < .05$ vs CNP group
SHR spontaneous hypertensive rat
VNP vasonatrin peptide
MAP mean arterial pressure
HR heart rate
RAP right atrial pressure
UV urine volume
UNaV urine sodium excretion
UKV urine potassium excretion
PcGMP plasma cGMP
UcGMPV urine cGMP volume As shown by the data in Table 3, the baseline MAP of SHR was significantly higher than that of normal rats, and the baseline urine volume of SHR was markedly lower than that of normal rats. During high dose bolus infusion of VNP, MAP and RAP significantly decreased, urine flow, sodium excretion, plasma cGMP and urinary cGMP volume were significantly increased in both normal and SHR groups. While the lowering of MAP to VNP was similar in both groups, the renal actions and urinary cGMP effects of VNP were attenuated in SHR rats as compared to normal rats. VNP is a more potent, endothelium independent vasorelaxing peptide in both arteries and veins as compared to ANP and CNP. VNP also has a potent natriuretic effect in vivo.

EXAMPLE 2

Patients and Methods

The study protocol was in agreement with the guidelines of the Mayo Institutional Review Board. Informed consent was obtained from each patient and his or her family.

Study Subjects for Circulating DNP

Circulating DNP was assessed in 19 normal healthy human volunteers and 19 patients with heart failure. All patients with heart failure underwent a complete physical examination and laboratory evaluation and were categorized as class III or IV by New York Heart Association (NYHA) functional class criteria on the basis of their cardiac symptoms after physical examination. Causes of ventricular dysfunction in these patients with heart failure included idiopathic dilated cardiomyopathy and ischemic cardiomyopathy. All patients with heart failure were receiving standard cardiovascular treatment.

Quantification of Plasma DNP Concentration

Blood samples for the DNP assay were collected in chilled tubes that contained ethylenediaminetetraacetic acid and immediately placed on ice. After centrifugation at 2,500 rpm at 4° C. for 10 minutes, the plasma was decanted and stored at −20° C. until analyzed. Plasma (1 mL) was extracted on C-8 Bond Elute cartridges, which were washed with methanol and distilled water. DNP was eluted with 95% methanol that contained 1% trifluoroacetic acid. Concentrated eluates were then assayed with a specific and sensitive radioimmunoassay for DNP (Phoenix Pharmaceuticals, Mountain View, Calif.). Samples and standards were incubated with rabbit anti-DNP at 4° C. for 24 hours. $^{125}$I-labeled DNP (100 µL) was added, and incubation was continued for another 24 hours at 4° C. Free and bound fractions were then separated by addition of a second antibody and normal rabbit serum and centrifuged. Radioactivity of the bound fraction was measured with a gamma counter. The minimal detectable level for this assay is 0.5 pg per tube, and the 50% inhibitory concentration of the standard curve was 29.0 pg. Recovery was 83.0±1.8%, and intra-assay variation was 10.0±3.2%. No cross-reactivity of the antibody to DNP was noted with ANP, BNP, CNP, or endothelin.

Study Subjects for DNP Immunohistochemistry

Human cardiac tissue for immunohistochemical studies was obtained from the atrial myocardium of four patients with end-stage CHF who were undergoing cardiac transplantation at Mayo Clinic, Rochester. The causes of CHF included idiopathic dilated cardiomyopathy and ischemic cardiomyopathy. Tissue sections were obtained from the atrial appendages and free walls. Normal atrial tissue was obtained from three donor hearts at the time of cardiac transplantation.

Immunohistochemical Staining

Immunohistochemical studies were performed by the indirect immunoperoxidase method as described previously by Wei et al. (1993). Tissues were immediately fixed with 10% buffered formalin and embedded in paraffin; sections 6 µm thick were cut and mounted on silanized glass slides. The slides were incubated at 60° C. and deparaffinized with graded concentrations of xylene and ethanol. To block the activity of endogenous peroxidase, we incubated the slides with 0.6% hydrogen peroxide in methanol for 20 minutes at room temperature. After being washed, sections were incubated in 5% goat serum (Dako Corp., Carpinteria, Calif.) for 10 minutes at room temperature to reduce non-specific background staining, and they were then incubated with polyclonal rabbit anti-DNP (Phoenix Pharmaceuticals) antiserum at a dilution of 1:500 (in normal goat serum) in humidified chambers for 24 hours at room temperature. All slides were incubated for 30 minutes with a second antibody-horseradish peroxidase conjugate (BioSource, Camarillo, Calif.). The reaction was visualized by incubating the sections with freshly prepared reagent that contained 3'-amino-9'-ethylcarbazole (Sigma Chemical Company, St. Louis, Mo.) in dimethylformamide and sodium acetate. The sections were counter-stained with hematoxylin, coverslipped, and reviewed with use of an Olympus microscope. Six independent observers, without knowledge of the respective groups from which these tissues originated, reviewed these sections. The presence of DNP-LI was quantified on the basis of the following scale of staining: 0=none; 1=minimal density; 2=mild density; 3=moderate density; and 4=maximal density. Control sections were stained with 1% non-immune goat serum.

Statistical Analysis

Data were recorded as mean values±standard error of the mean, unless otherwise indicated. Statistical comparisons between groups were performed with use of Student's unpaired t test by using Graph Pad prism software. P values of less than 0.05 were considered to be statistically significant.

Results

DNP-LI in Plasma of Normal Subjects and Patients with CHF

Figure 2:
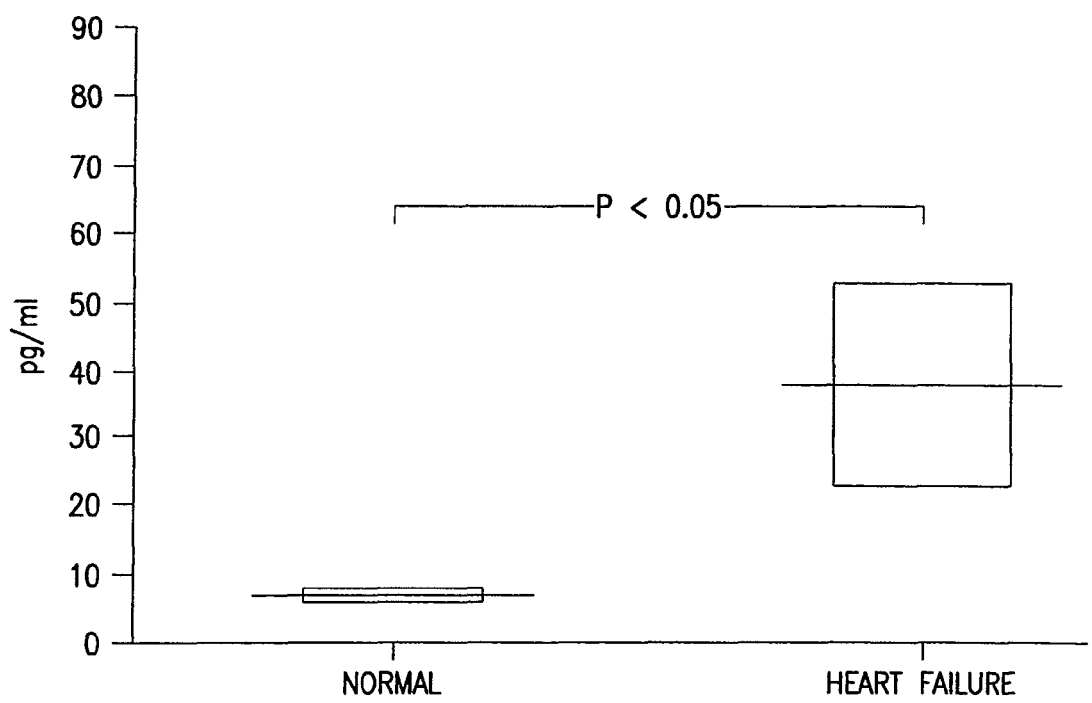
FIG. 2 is a box-plot of plasma *Dendroaspis* natriuretic peptide-like immunoreactivity in normal human volunteers (N=19) and humans with heart failure (N=19) (class NYHA III and IV; Schirger et al., 1999). Middle horizontal lines=means; vertical bars=standard error of mean.

In a study of 19 normal volunteers, DNP-LI was found to be present in normal human plasma (mean, 6.3±1.0 pg/mL; median, 4.7; standard deviation, 2.3). Furthermore, plasma DNP-LI was noted to be increased in 19 humans with CHF in comparison with the normal control subjects (mean, 37.3±15.0 pg/mL; median, 17.0; standard deviation, 58.9; P<0.05) (FIG. 2).

Figures 3A, 3B, 3C:
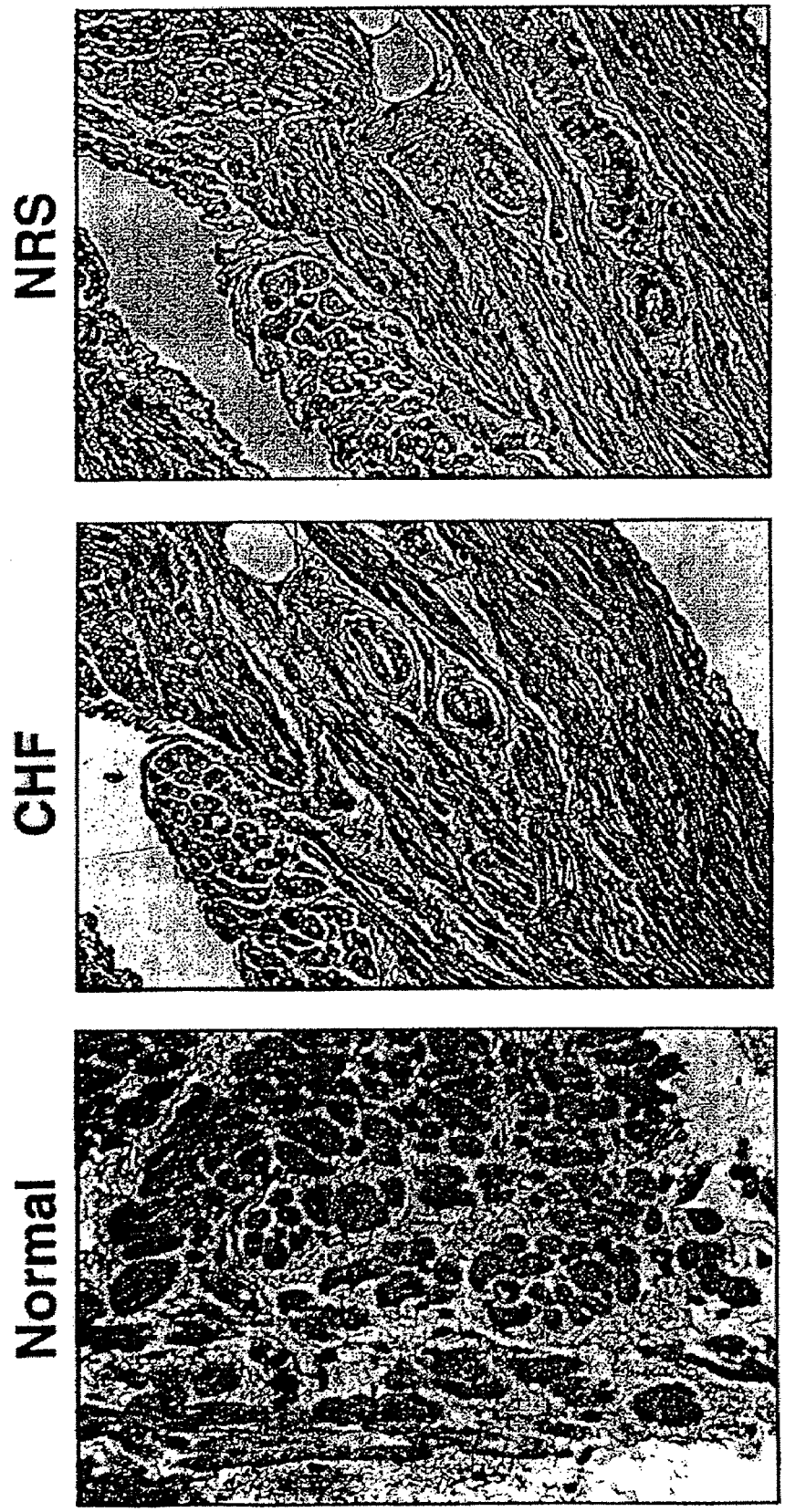
FIG. 3(A-C) shows immunostaining for *Dendroaspis* natriuretic peptide. Left (3A), normal human heart. Middle (3B), human with congestive heart failure (CHF). Right (3C), staining with nonimmune response serum (NRS) from same heart as shown in middle panel (original magnification, $X_{400}$).
Figure 4B:
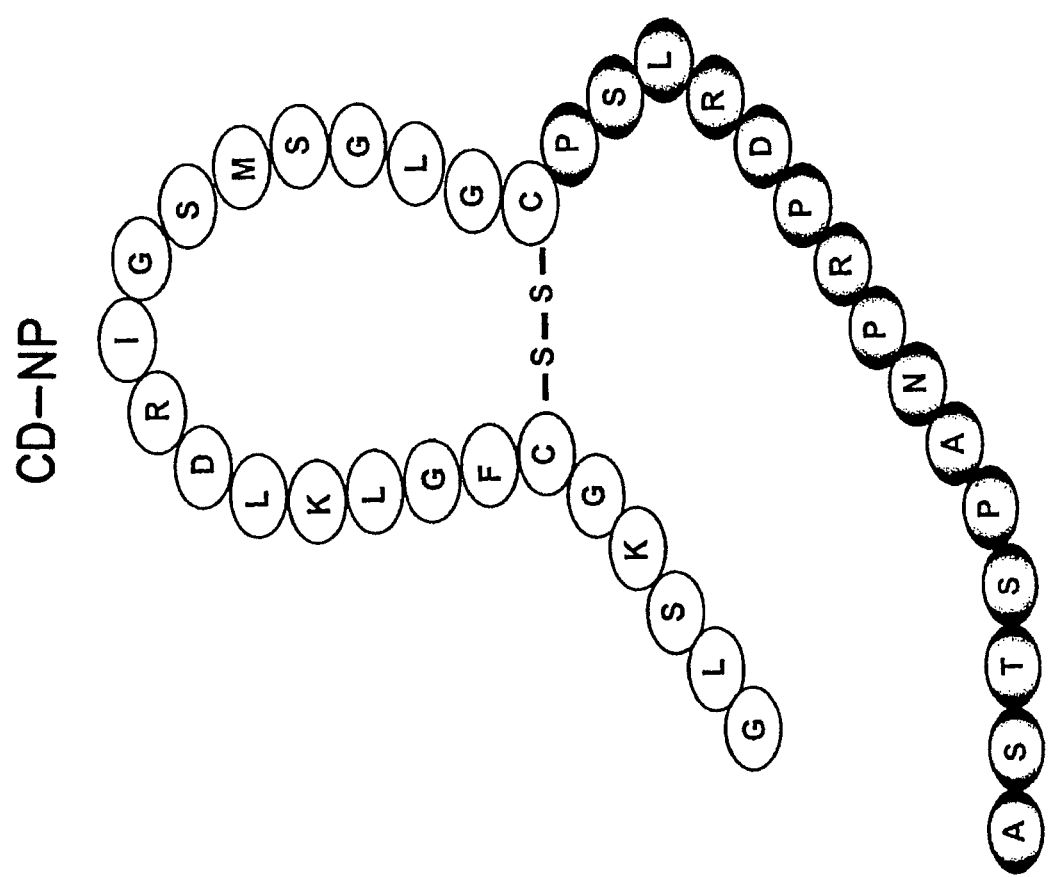
FIG. 4(A-C) depicts the amino acid sequence of exemplary peptides of the invention (SEQ ID NOS: 1-3).
Figure 4C:
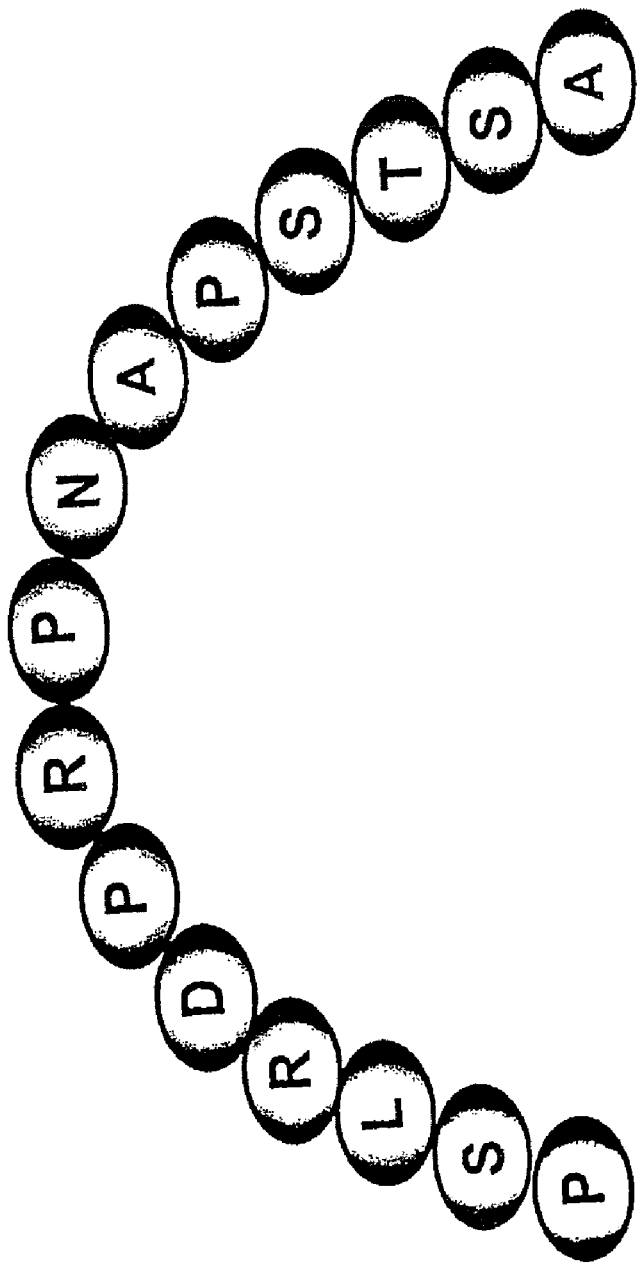
Figure 5:
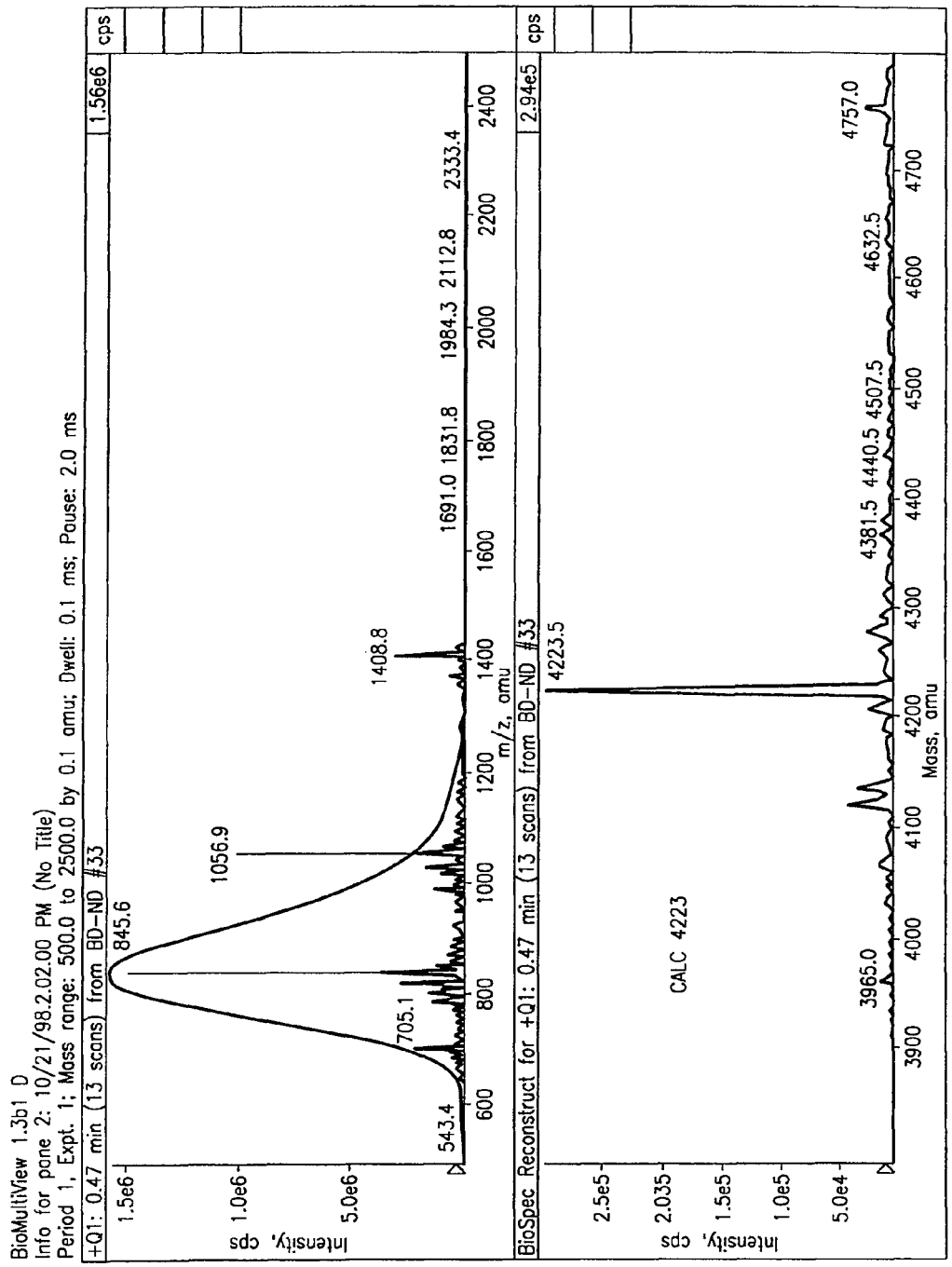
FIG. 5 illustrates the detection of BD-NP by high-performance liquid chromatography (HPLC).
Figure 6:
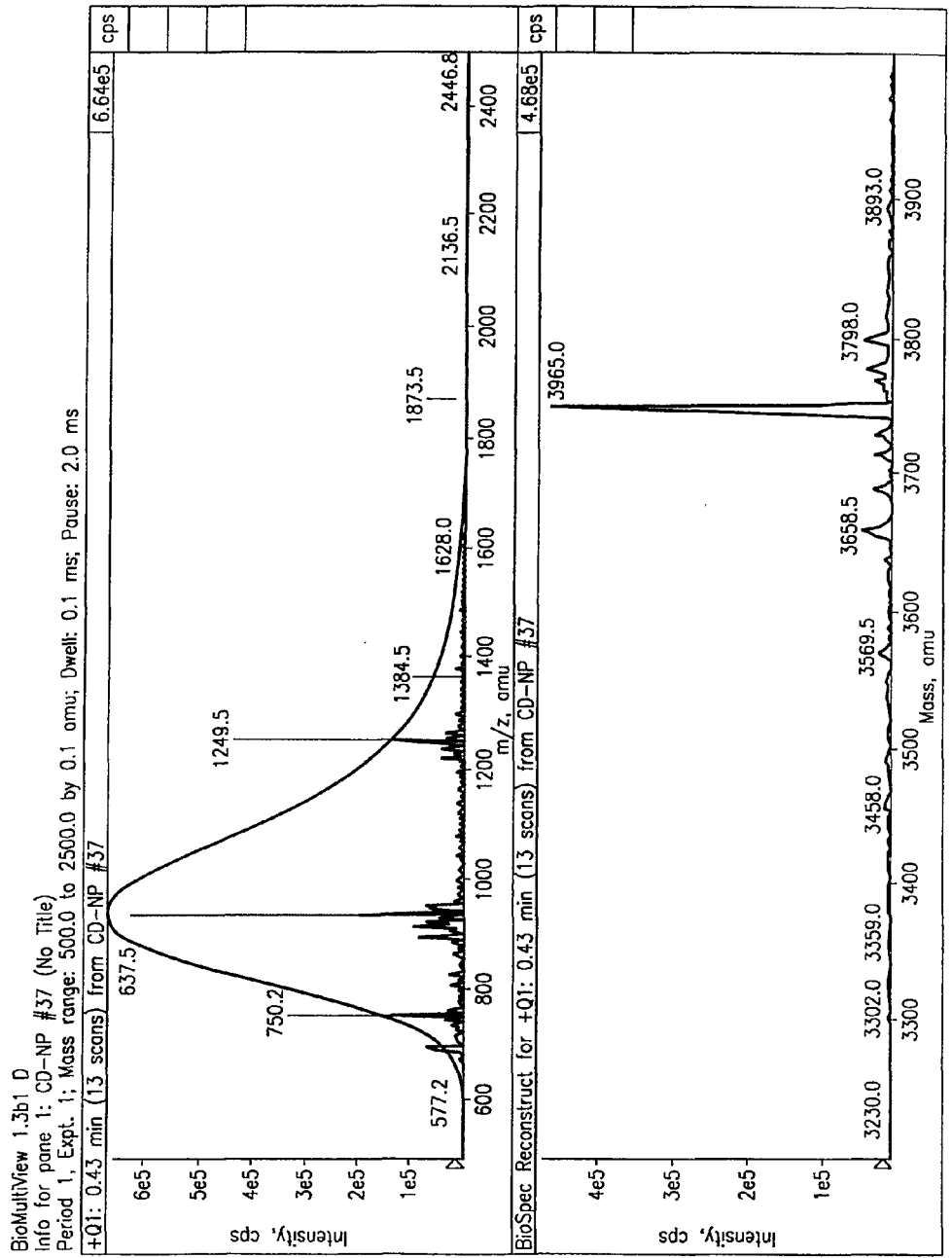
FIG. 6 shows the detection of CD-NP by HPLC.
Figure 7:
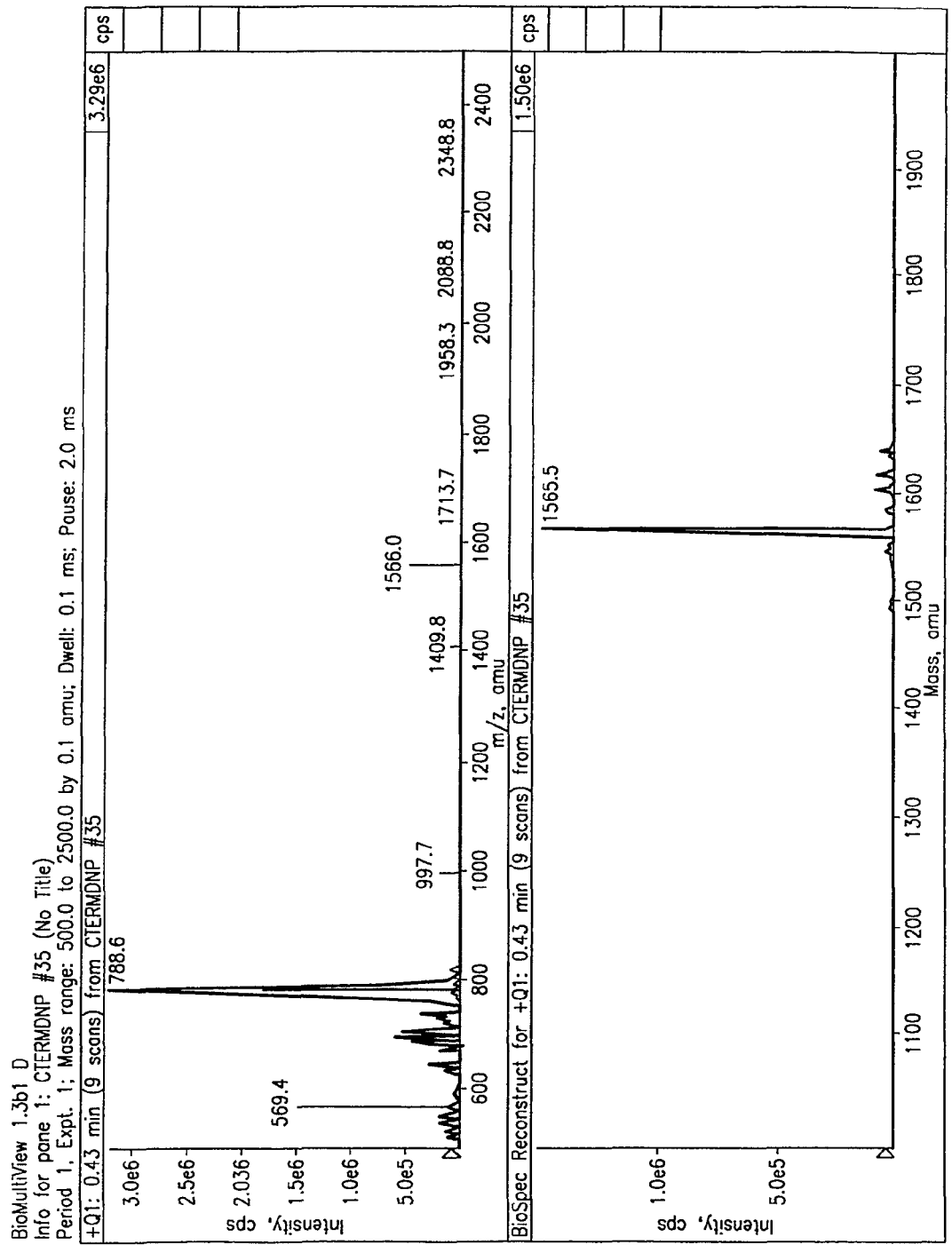
FIG. 7 illustrates the detection of the C-terminus of DNP by HPLC.

Immunohistochemical Studies of Myocardium of Normal Subjects and Patients with CHF Immunohistochemical studies revealed the presence of DNP-LI in the atrial myocardium of the normal and failing human heart (FIG. 3). DNP-LI was observed within the cytoplasm of atrial myocytes and was distributed widely in the peripheral cytoplasm. DNP-LI was also located in the perinuclear region. The immunohistochemical scores for DNP-LI in the atrial myocardium did not differ significantly in normal (N=3) and failing (N=4) human hearts (1.8±0.5 versus 2.2±0.7).

Discussion

Using a sensitive radioimmunoassay for DNP, which employs a polyclonal rabbit antibody to DNP that possesses no cross-reactivity with ANP, BNP, or CNP, DNP-LI was detected in normal human plasma. The concentrations noted were similar to those reported for the other natriuretic peptides (Mukoyama et al., 1991; Burnett et al., 1986; Wei et al., 1993). In addition, using this antibody to DNP, the presence and distribution of DNP-LI in the human atrial myocardium was determined. DNP-LI, similar to ANP and BNP, was observed to be present and widely distributed in the peripheral cytoplasm of atrial myocytes and also in the perinuclear region (Wei et al., 1993). Collectively, the presence of DNP-LI in human plasma and atrial myocardium suggests that DNP, like ANP and BNP, may be produced and secreted by the human heart.

An additional major finding was that plasma DNP-LI was increased in humans with CHF, specifically in patients categorized in NYHA class III or IV. This increase in plasma concentration of DNP-LI is analogous to that seen with ANP and BNP, which are activated in chronic CHF secondary to increased cardiac filling pressures and atrial stretch (Bruneau et al., 1997; Edwards et al., 1988). The increased concentration of DNP-LI in human CHF, together with the vasorelaxing properties of DNP in the rat aorta and canine coronary arteries as well as the potentiation of cGMP by DNP in vitro, suggests that, like ANP and BNP, the DNP-LI increase may be part of a compensatory neurohumoral response of the failing heart to maintain cardiovascular homeostasis (Schweitz et al., 1992; Wennberg et al., 1997). Moreover, the presence of DNP-LI in the plasma may, like ANP and BNP, have diagnostic potential in left ventricular dysfunction (Stevens et al., 1995; Yamamoto et al., 1997; McDonagh et al., 1998).

Atrial levels of DNP-LI immunohistochemical staining reported in these studies did not differ in CHF in comparison with normal atria. This finding suggests similarities to ANP, which is present in similar concentrations in normal and in failing human atrial myocardium as a result of increased production and secretion by the failing myocardium leading to increased circulating ANP in CHF (Bruneau et al., 1997). Production and secretion of DNP by the atrial myocardium in human CHF may account for the increased plasma concentration of DNP-LI in the absence of any changes in DNP-LI in the atria, as detected by immunohistochemical studies. Alternatively, increases in circulating DNP-LI may also involve reduced hepatic and renal clearance attributable to impaired hepatic and renal function in humans with CHF. Furthermore, although the current studies, which used a polyclonal antibody (with no cross-reactivity to ANP, BNP, CNP, or endothelin) to a DNP amino acid sequence isolated from snake venom, suggest the existence of DNP in the plasma and atria of humans, further investigations are needed to characterize human DNP more specifically and to synthesize its precise species-specific amino acid sequence.

EXAMPLE 3

The known natriuretic peptides ANP, BNP and CNP have potent biological actions including natriuresis, diuresis, vasodilatation and anti-mitogenesis. As chimeric peptides, BD-NP and CD-NP, and the C-terminus of DNP, may share some of the properties of ANP, BNP and CNP as well as some unique characteristics, the in vivo properties of BD-NP, CD-NP and the C-terminus of DNP were assessed.

Methods

Studies were performed in seven male mongrel dogs weighing between 20 and 25 kg. Dogs were maintained on a normal-sodium diet with standard dog chow (Lab Canine Diet 5006; Purina Mills, St. Louis, Mo.) with free access to tap water. All studies conformed to the guidelines of the American Physiological Society and were approved by the Mayo Clinic Animal Care and Use Committee.

On the evening before the experiment, 300 mg of lithium carbonate were administered orally for the assessment of renal tubular function, and dogs were fasted overnight. On the day of the acute experiment, all dogs were anesthetized with pentobarbital sodium given intravenously (30 mg/kg). Supplemental nonhypotensive doses of pentobarbital sodium were given as needed during the experiment. After tracheal intubation, dogs were mechanically ventilated (Harvard respirator; Harvard Apparatus, Millis, Mass.) with 4 L/minute of supplemental oxygen.

Left lateral flank incisions were made, and the left kidney was exposed via a retroperitoneal approach. The ureter was cannulated with polyethylene catheters (PE-200) for a timed urine collection, and a calibrated non-cannulating electromagnetic flow probe was placed carefully around the left renal artery and connected to a flowmeter (model FM 5010, Caroline Medical Electronics, King, N.C., USA) for continuous monitoring of renal blood flow (RBF). Finally, the right femoral vein was cannulated with two polyethylene catheters (PE-24), one for infusion of inulin and the other for the infusion of a peptide of the invention, e.g., BD-NP. The right femoral artery was cannulated with a polyethylene catheter (PE-240), for direct arterial blood pressure measurement and arterial blood sampling.

After completion of the surgical preparation, a priming dose of inulin (ICN Biomedicals, Cleveland, Ohio, USA) dissolved in isotonic saline solution was injected, followed by a constant infusion of 1 ml/minute to achieve a steady-state plasma inulin concentration between 40 and 60 mg/dl. The dogs were placed in dorsal suspension and allowed to equilibrate for 60 minutes without intervention. Body temperature was maintained by external warming (infrared heating lamp).

After an equilibration period of 60 minutes, a 30 minute baseline clearance (baseline) was performed. This was followed by a 15 minute lead-in period, during which BD-NP infusion at 10 ng/kg/minute was begun intravenously, after which the second 30 minute clearance period was performed. After the second clearance period, the intravenous infusion of BD-NP was changed to 50 ng/kg/minute. After a 15 minute lead-in period with this dose of BD-NP, a 30 minute clearance was performed. At the end of the third clearance, the infusion was stopped and a 30 minute washout period followed with a 30 minute recovery clearance (recovery).

Analytical Methods

Plasma for electrolyte and inulin measurements was obtained from blood collected in heparinized tubes. Plasma and urine electrolytes including lithium were measured by flame-emission spectrophotometer (IL943, Flame Photometer; Instrumentation Laboratory, Lexington, Mass.). Plasma and urine inulin concentrations were measured by the anthrone method, and the glomerular filtration rate (GFR) was measured by the clearance of inulin. The lithium clearance technique was employed to estimate the proximal and distal fractional reabsorption of sodium. Proximal fractional reabsorption was calculated by the following formula: [1−(lithium clearance/GFR)]×100. Distal fractional reabsorption of sodium was calculated by this formula: [(lithium clearance−sodium clearance)/lithium clearance]×100.

Plasma and urinary cGMP were measured by radioimmunoassay using the method of Steiner et al. (1972). Urine for cGMP measurement was heated to 90° C. before storage at −20° C. to inhibit degradative enzymatic activity.

Results

In the first study, the cardiorenal and humoral actions of parenterally administered BD-NP, which has the core structure of BNP and C-terminus of DNP, was assessed. The therapeutic potential of BD-NP upon cardiorenal and endocrine function was determined in 7 normal anesthetized dogs. Intravenous BD-NP was infused after baseline measurements at 10 and 50 ng/kg/min.

Administration of BD-NP resulted in a decrease in MAP (133±5 to 123±4 and 106±3* mmHg; *p<0.05 vs. Baseline)), RAP (3.0±0.4 to 1.8±0.3* and 1.2±0.3* mmHg), PAP (16.6±0.7 to 15.1±0.5* and 12.4±0.3* mmHg) and pulmonary capillary wedge pressure (PCWP) (5.3±0.4 to 3.6±0.4* and 2.0±0.4* mmHg). Glomerular filtration rate (GFR) increased (30±2 to 45±4* and 45±4* ml/minute) without changes in renal blood flow (RBF). Thus, BD-NP had a significant diuretic (UV: 0.24±0.1 to 1.12±0.3 and 2.17±0.5* ml/minute) and natriuretic effect (UNaV: 12.7±18 to 105.1±44* and 181.7±52* mEq/minute) with a decrease in proximal fractional reabsorption of sodium (PFRNa) (84.9±4.3 to 66.5±3.8* and 59.0±4.1*%). Plasma cGMP (11±1.5 to 26±2.5* and 45±4.9* pmol/ml) and urinary cGMP excretion (1414±164 to 3044±269 and 10840±1872* μmol/ minute) during BD-NP administration markedly increased. Both doses of BD-NP decreased plasma renin activity significantly (8.9±1 to 3.9±0.6* and 5.1±1.1* ng/ml/hour).

Thus, BD-NP potently reduces cardiac filling pressures, augments diuresis and natriuresis and possesses renin-suppressing actions. These findings support a possible role for this chimeric peptide in the treatment of CHF.

The second peptide, CD-NP, which shares the core structure of CNP and C-terminus of DNP, was tested in a different group of dogs but under the same experimental conditions. Administration of CD-NP at the same dose (10 and 50 ng/kg/min) resulted in a decrease in MAP (135 to 133 and 125 mmHg), RAP (3.0 to 2.8 and 2.0 mmHg), PAP (13.5 to 13.0 and 12.5 mmHg) and PCWP (8.0 to 6.0 and 5.0 mmHg) with an increase in GFR (38 to 47 and 49 ml/minute). These changes were associated with a decrease in systemic vascular resistance during the administration of low dose DNP(SVR: 39 to 33 mmHg/l/minute). CD-NP had a diuretic (UV: 0.14 to 0.27 and 1.01 ml/minute) and natriuretic effect (UNaV: 3.4 to 14.2 and 63.8 µEq/minute) with a decrease in PFRNa (87 to 73 and 61%). Plasma cGMP (11 to 15 and 35 pmol/ml) and urinary cGMP excretion (1931 to 2844 and 7551 pmol/minute) during CD-NP administration markedly increased. Thus, the administration of CD-NP potently reduces cardiac filling pressures and augments diuresis and natriuresis. These actions are associated with the activation of the cGMP system.

A third peptide, i.e., the C-terminus of DNP, was tested in vivo in another group of normal anesthetized dogs. Administration of the C-terminus of DNP (same dose) resulted in a diuresis (UV: 0.55 to 0.70 and 1.83 ml/minute) and natriuresis (UNaV: 64 to 75 and 123 µEq/minute) with a decrease in PFRNa (67 to 58 and 56%). There was an increase in GFR during administration of the higher dose (36 to 36 and 41 ml/minute). These effects of C-terminus of DNP were associated with an increase in plasma cGMP (7 to 11 and 12 pmol/ml) and urinary cGMP excretion (1538 to 1842 and 1786 µmol/minute) but no changes in the cardiovascular hemodynamics were observed. However, both doses of C-terminus of DNP decreased plasma renin activity (4.0 to 1.8 and 1.9 ng/ml/hour). Thus, the C-terminus DNP has natriuretic, diuretic and renin-suppressing properties when administered to canines.

EXAMPLE 4

Methods

To determine the cardiorenal and endocrine properties of the peptides of the invention in CHF, an animal model for mild and overt CHF is employed. Studies are performed in three groups of male mongrel dogs. The first group consists of normal dogs (normals; n=5), the second group consists of dogs with mild heart failure induced by rapid ventricular pacing at 180 bpm for 10 days (mild CHF; n=7), and the third group consists of dogs with overt heart failure induced by rapid ventricular pacing at 245 bpm for 10 days (overt CHF, n=7). Dogs are maintained on fixed sodium diet (Hill's Prescription Diet, Canine i/d) with free access to tap water. All studies conform the guidelines of the American Physiological Society and were approved by the Mayo Clinic Animal Care and Use Committee.

Pacemaker Implantation

Dogs from the second and third group are first anesthetized utilizing pentobarbital sodium (30 mg/kg, i.v.) two weeks prior to the protocol. After tracheal intubation, dogs are mechanically ventilated utilizing a Harvard respirator (Harvard Apparatus, Millis, Mass.) with 4 L/minute of supplemental oxygen. An epicardial lead (Medtronic, Minneapolis, Minn.) is implanted on the right ventricle via a left thoracotomy with a 1-2 cm pericardiotomy. The pacemaker lead is connected to a pulse generator (Medtronic, Minneapolis, Minn., model 8329) which is then implanted subcutaneously in the chest wall. Pacing capture is verified intraoperatively prior to closing the chest cavity. The pericardium is sutured closed with great care not to distort the anatomy of the pericardium. The chest cavity, deep and superficial incisions are then closed in layers. Dogs receive pre- and post-operative prophylactic antibiotic treatment with 225 mg clindamycin subcutaneously and 400,000 U procaine penicillin G plus 500 mg dihydrostreptomycin intramuscularly (Combiotic, Pfizer, Inc., New York, N.Y.). The prophylactic antibiotic treatment is continued through the first two postoperative days.

Following a 14 day post-operative recovery period, mild CHF is produced by rapid ventricular pacing at 180 bpm for 10 days. Overt CHF is produced by rapid ventricular pacing at 245 bpm for 10 days.

Acute Protocol

The following acute protocol is performed in all three groups. On the night before the acute experiment the animals are fasted, given 300 mg of lithium carbonate for the assessment of renal tubular functions and allowed free access to water. On the day of the acute experiment (11th day of pacing in the heart failure groups), all dogs are anesthetized with pentobarbital sodium given intravenously (15 mg/kg). Supplemental non-hypotensive doses of pentobarbital sodium are given as needed during the experiment. After tracheal intubation, dogs are mechanically ventilated (Harvard respirator, Millis, Mass.) with 4 L/minute of supplemental oxygen. A flow-directed balloon-tipped thermodilution catheter (Ohmeda, Criticath, Madison, Wis.) is advanced into the pulmonary artery via the external jugular vein for cardiac hemodynamic measurements. A left lateral flank incision is made and the left kidney was exposed via a retroperitoneal approach.

The ureter is cannulated with polyethylene catheters (PE-200) for timed urine collection, and a calibrated noncannulating electromagnetic flow probe is placed carefully around the left renal artery and connected to a flowmeter (model FM 5010, King, N.C.) for continuous monitoring of renal blood flow (RBF). Finally, the right femoral vein is cannulated with two polyethylene catheters (PE-240), one for infusion of inulin and the other for the infusion of a natriuretic peptide (NP) of the invention. The right femoral artery is cannulated with a polyethylene catheter (PE-240) for direct arterial blood pressure measurement and arterial blood sampling. After completion of the surgical preparation, a priming dose of inulin (ICN Biomedicals, Cleveland, Ohio) dissolved in isotonic saline solution is injected, followed by a constant infusion of 1 mL/minute to achieve a steady-state plasma inulin concentration between 40 and 60 mg/dL. The dogs are placed in dorsal suspension and allowed to equilibrate for 60 minutes without intervention. Body temperature is maintained by external warming.

After an equilibration period of 60 minutes, a 30 minute baseline clearance (Baseline) is performed. This is followed by a 15 minute lead-in period during which NP infusion at 10 ng/kg/minute is begun intravenously after which the second 30 minute clearance period is performed. After the second clearance period, the intravenous infusion of NP is changed to 50 ng/kg/minute. After a 15 minute lead-in period with this dose of NP a 30 minute clearance is performed. At the end of the third clearance, the natriuretic peptide infusion is stopped and a 90 minute washout period is followed with a 30 minute recovery clearance (Recovery).

Analytical Methods

Cardiovascular parameters measured during the acute experiment include mean arterial pressure (MAP), right atrial pressure (RAP), pulmonary artery pressure (PAP), cardiac output (CO) and pulmonary capillary wedge pressure (PCWP). CO is determined by thermodilution in triplicate and averaged (Cardiac Output computer, model 9510-A, American Edwards laboratories, Irvine, Calif.). MAP is assessed via direct measurement from the femoral arterial catheter. Systemic vascular resistance (SVR) is calculated as [SVR=(MAP−RAP)/CO]. Pulmonary vascular resistance (PVR) is calculated as [PVR=(PAP−PCWP)/CO].

Plasma for electrolyte and inulin measurements is obtained from blood collected in heparinized tubes. Plasma and urine electrolytes including lithium are measured by flame-emission spectrophotometer (IL943, Flame Photometer, Instrumentation Laboratory, Lexington, Mass.). Plasma and urine inulin concentrations are measured by the anthrone method, and glomerular filtration rate (GFR) is measured by the clearance of inulin. The lithium clearance technique is employed to estimate the distal fractional reabsorption of sodium. Proximal fractional reabsorption of sodium is calculated by the formula: [1−(lithium clearance/glomerular filtration rate)×100. Distal fractional reabsorption of sodium is calculated by the formula: [(lithium clearance−sodium clearance)/lithium clearance]×100. Renal vascular resistance (RVR) is calculated as [RVR=(MAP−RAP)/RBF]. Plasma and urinary cGMP is measured by radioimmunoassay using the method of Steiner et al. (1972). Urine for cGMP measurement is heated to 90° C. before storage at −20° C. to inhibit degradative enzymatic activity.

Plasma and urinary NP is determined utilizing a radioimmunoassay before, during and following the NP administration (Lisy et al., 1999a and Schirger et al., 1999).

Results for Synthetic DNP Administration

Baseline Characteristics

Figure 10:
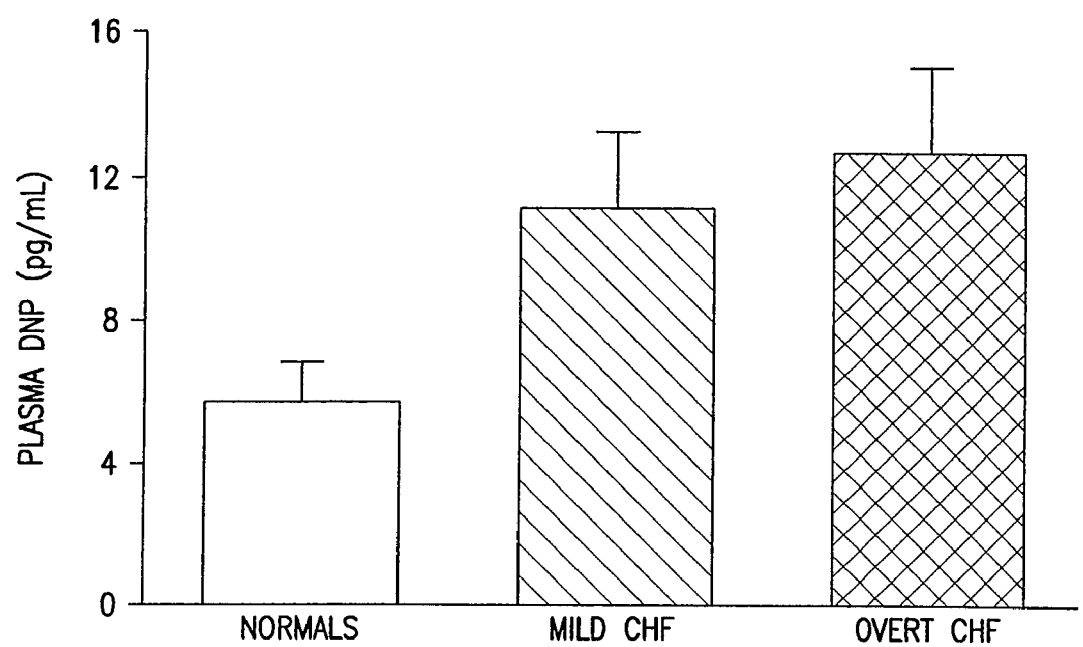
FIG. 10 shows the baseline plasma levels of DNP in normal, mild CHF and overt CHF dogs prior to the infusion of exogenous DNP. Open bar represents normals, hatched bar represents mild CHF and full bar represents overt CHF. Values are expressed as mean±SEM. *P<0.05 vs. normals.
Figure 11A:
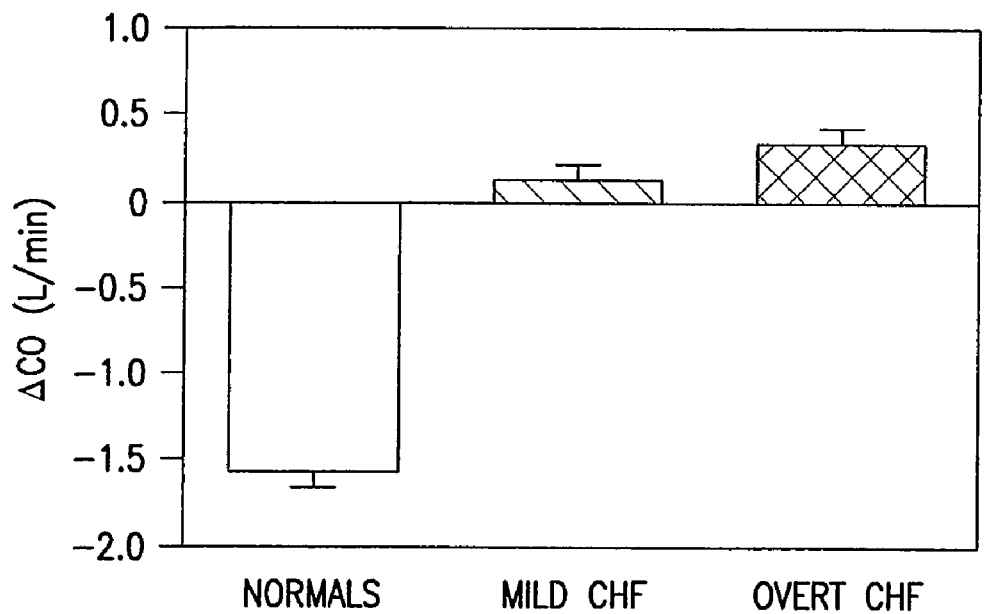
FIG. 11 depicts the maximal changes in cardiac output—ΔCO (A), systemic vascular resistance—ΔSVR (B), right atrial pressure—ΔRAP (C) and pulmonary capillary wedge pressure—ΔPCWP (D) during the administration of DNP. Open bar represents normals, hatched bar represents mild CHF and full bar represents overt CHF. Values are expressed as mean±SEM. *P<0.05 vs. normals.
Figure 11B:
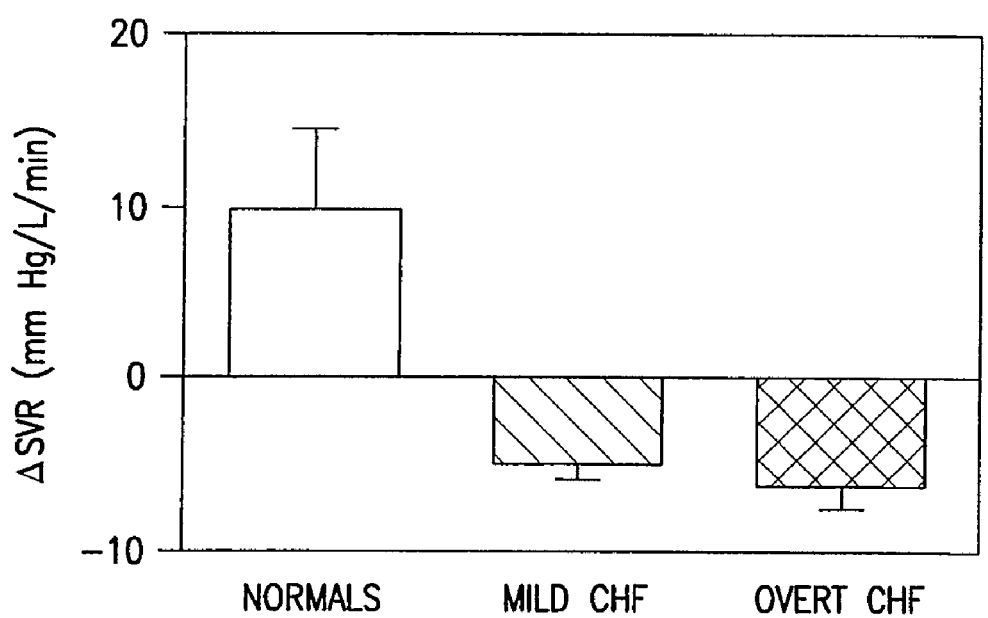
Figure 11C:
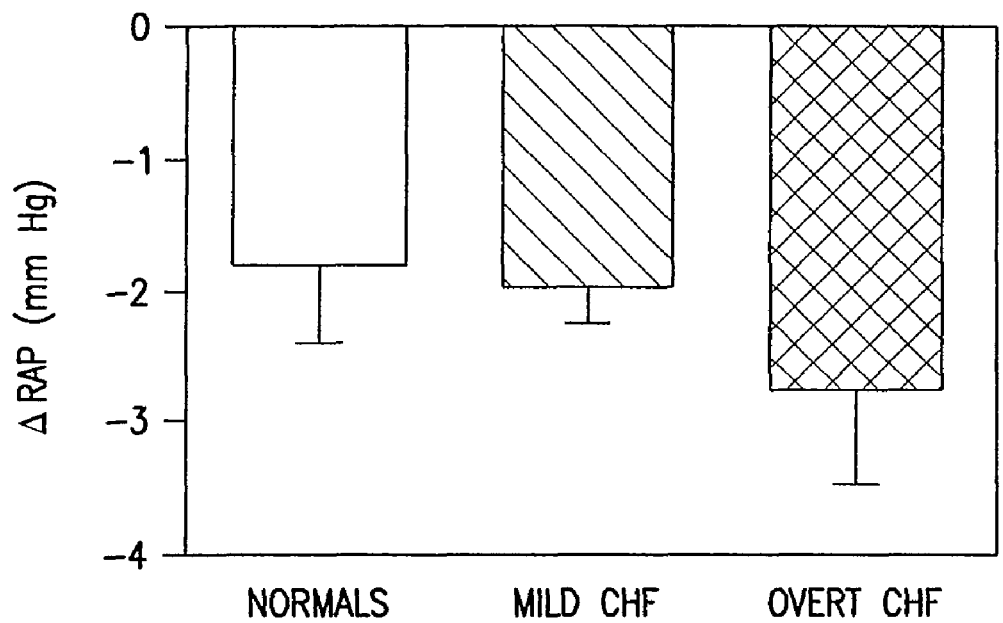
Figure 11D:
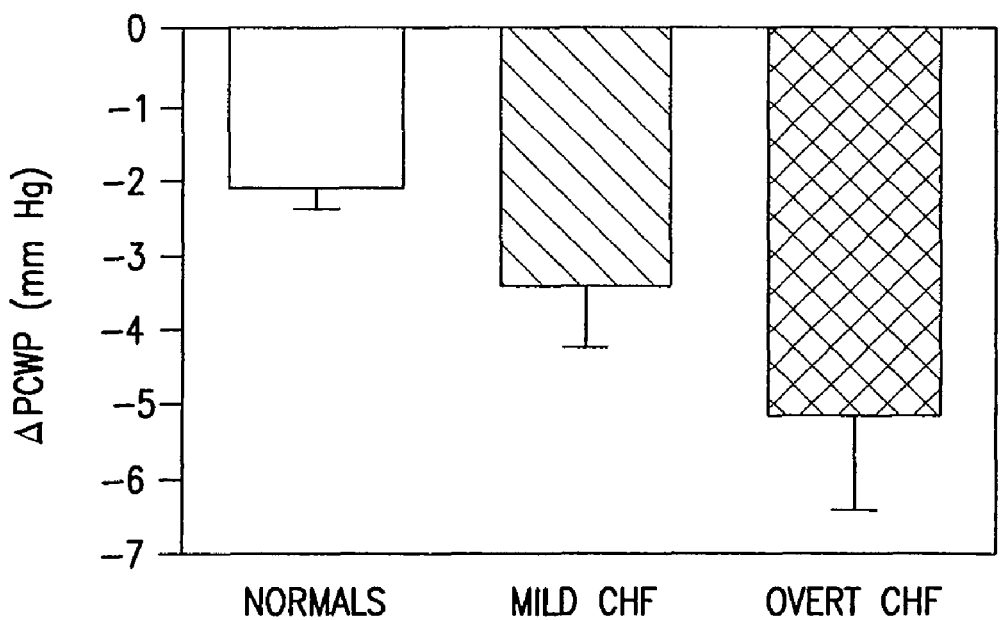

Baseline characteristics of all three groups are reported in Table 4. In mild CHF, MAP and CO were reduced, RAP and PCWP were increased. GFR and UNaV were decreased while plasma ANP was increased. In overt CHF, all these parameters were similarly changed in association with a further increase in RAP, PAP and PCWP and markedly decrease in UNaV. As illustrated in FIG. 10, the baseline levels of DNP-LI in mild and overt CHF prior to the infusion of exogenous DNP were higher than the plasma levels of DNP in normals.

TABLE 4

|  | Normals | Mild CHF | Overt CHF |
|---|---|---|---|
| MAP (mm Hg) | 146 ± 4 | 104 ± 3* | 101 ± 7* |
| CO (L/min) | 4.0 ± 0.2 | 2.5 ± 0.2* | 2.2 ± 0.1* |
| SVR (mmHg/L/min) | 36.5 ± 3 | 41.4 ± 3 | 40.5 ± 4 |
| RAP (mm Hg) | 0.3 ± 0.7 | 4.4 ± 0.6* | 9.2 ± 1.4*† |
| PAP (mm Hg) | 16.9 ± 1.0 | 20.3 ± 1.2 | 32.8 ± 2.7*† |
| PCWP (mm Hg) | 5.7 ± 0.4 | 13.3 ± 1.8* | 26.7 ± 2.1*† |
| GFR (mL/min) | 37 ± 3 | 27 ± 4* | 22 ± 1* |
| UNaV (μEq/min) | 70.0 ± 34 | 24.3 ± 12 | 1.8 ± 1* |
| ANP (pg/mL) | 17 ± 1 | 254 ± 54* | 359 ± 55* |
| PRA (ng/mL/hr) | 8 ± 2 | 9 ± 2 | 12 ± 1* |

MAP indicates mean arterial pressure; CO, cardiac output; SVR, systemic vascular resistance; RAP, right atrial pressure; PAP, pulmonary artery pressure; PCWP, pulmonary capillary wedge pressure; GFR, glomerular filtration rate; UNaV, urinary sodium excretion; ANP, atrial natriuretic peptide; PRA, plasma renin activity.
*$P < 0.05$ vs. Normals;
†$P < 0.05$ vs. Mild CHF.

Cardiovascular Hemodynamics During DNP Administration

Cardiovascular hemodynamics before and during DNP administration is reported in Table 5.

TABLE 5

|  | Baseline | DNP-10 | DNP-50 | Recovery |
|---|---|---|---|---|
| MAP (mmHg) | | | | |
| Normals | 146 ± 4 | 133 ± 7 | 111 ± 9* | 126 ± 9* |
| Mild CHF | 104 ± 3 | 96 ± 5 | 95 ± 6 | 105 ± 7 |
| Overt CHF | 101 ± 7 | 95 ± 6 | 89 ± 7* | 87 ± 13* |
| CO (L/min) | | | | |
| Normals | 4.0 ± 0.2 | 3.4 ± 0.2* | 2.5 ± 0.2* | 1.8 ± 0.1* |
| Mild CHF | 2.5 ± 0.2 | 2.6 ± 0.2 | 2.5 ± 0.2 | 1.8 ± 0.1* |
| Overt CHF | 2.2 ± 0.1 | 2.6 ± 0.1 | 2.1 ± 0.2 | 1.6 ± 0.1* |
| SVR (mmHg/L/min) | | | | |
| Normals | 37 ± 3 | 41 ± 4 | 47 ± 5 | 70 ± 5* |
| Mild CHF | 41 ± 3 | 37 ± 3 | 38 ± 3 | 56 ± 5* |
| Overt CHF | 41 ± 4 | 35 ± 3 | 38 ± 3 | 48 ± 7 |
| RAP (mmHg) | | | | |
| Normals | 0.3 ± 0.7 | −0.6 ± 0.4 | −1.5 ± 0.5* | −1.3 ± 0.6* |
| Mild CHF | 4.4 ± 0.6 | 3.1 ± 0.8* | 2.5 ± 0.8* | 4.4 ± 0.9 |
| Overt CHF | 9.2 ± 1.4 | 7.1 ± 1.1* | 6.5 ± 1.2* | 10.2 ± 0.9 |
| PCWP (mmHg) | | | | |
| Normals | 5.7 ± 0.4 | 4.4 ± 0.3* | 3.6 ± 0.2* | 4.5 ± 0.4* |
| Mild CHF | 13.3 ± 1.8 | 10.8 ± 2.4* | 9.9 ± 2.0* | 12.5 ± 2.1 |
| Overt CHF | 26.7 ± 2.1 | 23.0 ± 2.0* | 21.6 ± 1.5* | 21.3 ± 1.7* |
| PAP (mmHg) | | | | |
| Normals | 16.9 ± 1 | 15.3 ± 1* | 12.5 ± 0.4* | 12.8 ± 0.7* |
| Mild CHF | 20.3 ± 1 | 18.1 ± 1* | 16.5 ± 1* | 18.6 ± 1* |
| Overt CHF | 32.8 ± 3 | 28.9 ± 2* | 27.1 ± 2* | 30.2 ± 3* |
| PVR (mmHg/L/min) | | | | |
| Normals | 2.7 ± 0.2 | 3.2 ± 0.2 | 3.6 ± 0.1 | 4.6 ± 0.5* |
| Mild CHF | 3.6 ± 0.5 | 3.4 ± 0.4 | 3.1 ± 0.3 | 4.1 ± 0.4 |
| Overt CHF | 2.8 ± 0.4 | 2.4 ± 0.3 | 2.7 ± 0.4 | 5.5 ± 0.6* |

PVR, pulmonary vascular resistance.
*$P < 0.05$ vs Baseline

DNP administration resulted in reductions in MAP during the administration of higher dose of DNP in normals and overt CHF groups with a trend to decrease in MAP in mild CHF. While in overt CHF the hypotensive actions of DNP were sustained, MAP returned to the baseline after DNP administration in normals and in mild CHF. CO decreased in normals during DNP infusion, while in mild and overt CHF CO was preserved. RAP, PCWP and PAP decreased in all groups, particularly in both CHF groups in which were already markedly elevated at the baseline. There was a trend to decrease in SVR and PVR in both CHF groups during DNP administration.

The maximal changes in CO, SVR, RAP and PCWP during the administration of DNP are illustrated in FIG. 11. Panel A reports a significant upward trend in CO in both CHF groups compared to normals. Panel B illustrates significant downward trend in SVR also in both mild and overt CHF. The decrease in the cardiac filling pressures in all three groups in response to DNP is reported in Panels C and D.

Renal Hemodynamic and Excretory Function During DNP Administration

Table 6 reports renal hemodynamic and excretory function during DNP administration.

TABLE 6

|  | Baseline | DNP-10 | DNP-50 | Recovery |
|---|---|---|---|---|
| GFR (mL/min) | | | | |
| Normals | 37 ± 3 | 42 ± 5 | 40 ± 1 | 32 ± 7 |
| Mild CHF | 27 ± 4 | 44 ± 8* | 36 ± 3 | 29 ± 4 |
| Overt CHF | 22 ± 1 | 30 ± 3 | 33 ± 4* | 16 ± 7 |

TABLE 6-continued

|  | Baseline | DNP-10 | DNP-50 | Recovery |
|---|---|---|---|---|
| RBF (mL/min) | | | | |
| Normals | 305 ± 21 | 295 ± 16 | 313 ± 25 | 229 ± 30* |
| Mild CHF | 156 ± 16 | 156 ± 18 | 173 ± 21 | 136 ± 19 |
| Overt CHF | 112 ± 10 | 117 ± 9 | 121 ± 16 | 97 ± 14 |
| RVR (mmHg/L/min) | | | | |
| Normals | 0.49 ± 0.1 | 0.46 ± 0.1 | 0.37 ± 0.1 | 0.63 ± 0.2 |
| Mild CHF | 0.68 ± 0.1 | 0.68 ± 0.1 | 0.60 ± 0.1 | 0.87 ± 0.2 |
| Overt CHF | 0.89 ± 0.2 | 0.78 ± 0.1 | 0.77 ± 0.1 | 0.98 ± 0.3 |
| UNaV (µEq/min) | | | | |
| Normals | 70.0 ± 34 | 186.1 ± 57* | 246.0 ± 71* | 116.6 ± 44 |
| Mild CHF | 24.3 ± 12 | 66.5 ± 22 | 130.6 ± 30* | 69.6 ± 23 |
| Overt CHF | 1.8 ± 1 | 7.8 ± 4 | 31.6 ± 11* | 4.4 ± 2 |
| UV (mL/min) | | | | |
| Normals | 0.58 ± 0.2 | 1.73 ± 0.4 | 2.51 ± 0.7* | 1.30 ± 0.4 |
| Mild CHF | 0.26 ± 0.1 | 0.69 ± 0.2 | 1.85 ± 0.4* | 1.24 ± 0.3* |
| Overt CHF | 0.17 ± 0.1 | 0.33 ± 0.1 | 0.84 ± 0.3* | 0.09 ± 0.04 |
| PFRNa (%) | | | | |
| Normals | 65.3 ± 7.5 | 62.0 ± 7.1 | 61.0 ± 3.3 | 75.6 ± 5.3 |
| Mild CHF | 77.6 ± 4.0 | 70.2 ± 4.3 | 59.4 ± 2.6* | 73.2 ± 3.4 |
| Overt CHF | 87.7 ± 4.1 | 83.3 ± 4.1 | 64.1 ± 11.3* | 84.4 ± 4.5 |
| DFRNa (%) | | | | |
| Normals | 97.1 ± 1.1 | 92.7 ± 1.7 | 89.9 ± 2.3* | 91.6 ± 2.2* |
| Mild CHF | 95.2 ± 3.8 | 91.6 ± 5.7 | 90.4 ± 4.1 | 94.5 ± 1.7 |
| Overt CHF | 99.1 ± 0.6 | 99.4 ± 0.2 | 98.2 ± 0.6 | 98.1 ± 0.7 |

RBF, renal blood flow; RVR, renal vascular resistance; UV, urine flow; PFRNa, proximal fractional reabsorption of sodium; DFRNa, distal fractional reabsorption of sodium.
*P < 0.05 vs Baseline DNP administration in mild and overt CHF increased GFR, an action not observed in normals, in the absence of changes in RBF. DNP increased UNaV in normals and in mild overt CHF groups during the high dose DNP. Although the natriuretic action of DNP was attenuated in overt CHF, the increase in sodium excretion occurred despite significant reductions in MAP in overt CHF. High dose DNP also resulted in a significant diuretic response in all groups. In mild and overt CHF, DNP decreased PFRNa while DFRNa only decreased in normals.

Humoral Functions During DNP Administration

Table 7 reports hormonal response to DNP administration.

TABLE 7

|  | Baseline | DNP-10 | DNP-50 | Recovery |
|---|---|---|---|---|
| DNP (pg/ml) | | | | |
| Normals | 5.7 ± 1.2 | 274 ± 37 | 3582 ± 715* | 163 ± 9 |
| Mild CHF | 11 ± 2 | 306 ± 78 | 1084 ± 225* | 83 ± 14 |
| Overt CHF | 13 ± 2 | 463 ± 146* | 1060 ± 177* | 125 ± 22 |
| UDNPV (pg/min) | | | | |
| Normals | 21 ± 6 | 303 ± 110 | 1523 ± 239* | 204 ± 50 |
| Mild CHF | 31 ± 11 | 308 ± 67 | 887 ± 217* | 204 ± 46 |
| Overt CHF | 28 ± 7 | 339 ± 155 | 1713 ± 876* | 312 ± 83 |
| cGMP (pmol/mL) | | | | |
| Normals | 11 ± 1 | 38 ± 7* | 74 ± 5* | 42 ± 2* |
| Mild CHF | 31 ± 9 | 47 ± 4* | 72 ± 5* | 51 ± 5* |
| Overt CHF | 35 ± 6 | 46 ± 6 | 70 ± 10* | 46 ± 9 |
| UcGMPV (pmol/min) | | | | |
| Normals | 1079 ± 133 | 3798 ± 790 | 12430 ± 1238* | 3824 ± 750 |
| Mild CHF | 1478 ± 279 | 3507 ± 577 | 7420 ± 1810* | 3426 ± 505 |
| Overt CHF | 1685 ± 215 | 2325 ± 307 | 5081 ± 1002* | 1290 ± 333 |
| ANP (pg/mL) | | | | |
| Normals | 17 ± 1 | 18 ± 1 | 18 ± 2 | 15 ± 2 |
| Mild CHF | 254 ± 53 | 217 ± 47 | 232 ± 51 | 240 ± 45 |
| Overt CHF | 359 ± 55 | 296 ± 42 | 299 ± 42 | 301 ± 42 |
| PRA (ng/mL/hr) | | | | |
| Normals | 8.3 ± 1.8 | 3.7 ± 1.5* | 7.2 ± 1.7 | 6.8 ± 1.9 |
| Mild CHF | 8.7 ± 2.0 | 7.4 ± 2.6 | 7.9 ± 1.7 | 9.5 ± 1.2 |
| Overt CHF | 11.9 ± 1.0 | 9.0 ± 1.6* | 10.1 ± 1.5 | 8.9 ± 1.4* |

UDNPV, urinary DNP excretion; cGMP, cyclic guanosine monophosphate; UcGMPV, urinary cGMP excretion; ANP, atrial natriuretic peptide.
*P < 0.05 vs Baseline Plasma and urinary DNP increased during the administration of DNP in all groups. DNP significantly increased plasma cGMP in all groups, while the increase in urinary cGMP excretion was significant only during the administration of high dose of DNP. Plasma ANP or BNP did not increase during the administration of DNP in any of the three groups. Low dose of DNP resulted in a significant decrease in PRA in normals and in overt CHF.

Figure 12:
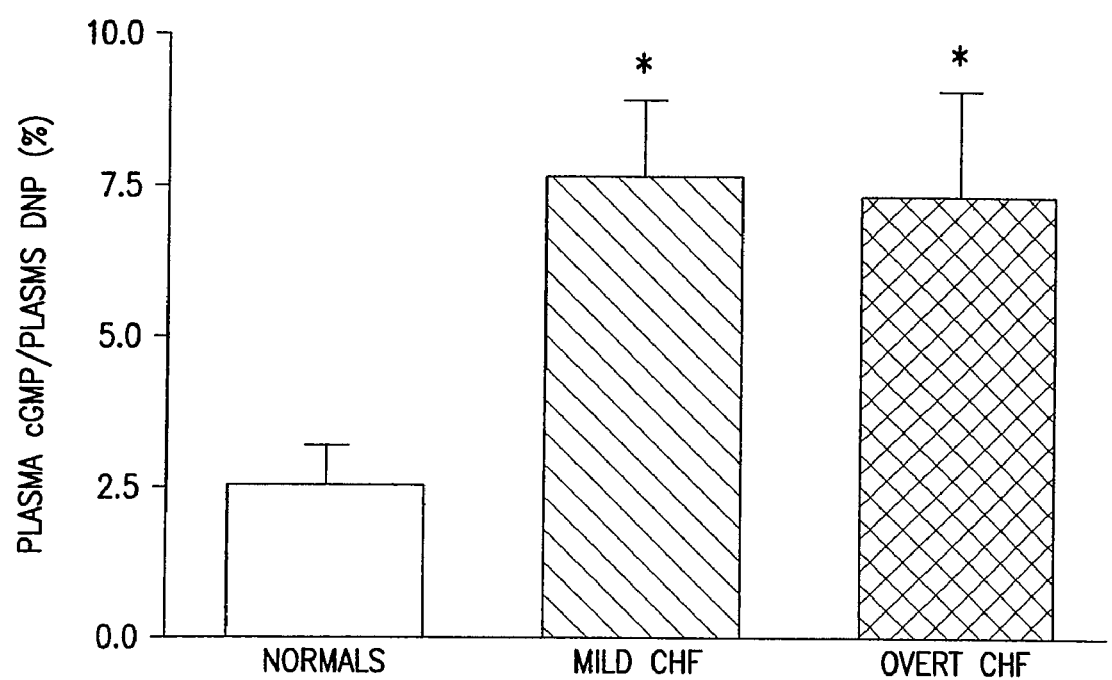
FIG. 12 shows the ratio of plasma cGMP/plasma DNP with high dose DNP in normal, mild CHF and overt CHF dogs. Open bar represents normals, hatched bar represents mild CHF and full bar represents overt CHF. Values are expressed as mean±SEM. *P<0.05 vs. normals.

In addition, the ratio of plasma cGMP/plasma DNP with high dose DNP was calculated for all three groups (FIG. 12). The ratio was higher for the CHF groups compared to normals supporting an enhanced cGMP generation by DNP in CHF.

Discussion

The current study demonstrates that exogenous administration of DNP in experimental mild and overt CHF has beneficial cardiovascular, renal and humoral actions. Specifically, DNP in mild and overt CHF decreased markedly elevated cardiac filling pressures and preserved cardiac output. Secondly, DNP increased glomerular filtration rate in CHF in the absence of changes in renal blood flow. In addition, DNP was natriuretic, although this action was attenuated in overt CHF. The natriuresis was also associated with a reduction in proximal tubular reabsorption of sodium despite reductions in renal perfusion pressure. The renal actions were further associated with reductions in plasma renin activity at low dose in overt CHF. Finally, the actions of DNP were associated with an enhanced ability to increase plasma cGMP in CHF.

A major finding was the ability of DNP to decrease markedly elevated cardiac filling pressures. This action was associated with a trend for cardiac output to increase and for systemic vascular resistance to decrease which were not seen in normals. Such an acute hemodynamic response is most consistent with reductions in preload in association with a modest peripheral arterial dilatation. The reduction in cardiac filling pressures occurred immediately and therefore was most likely due to a direct vascular action independent of the renal natriuretic response. Further, as plasma ANP tended to decrease consistent with decreased secretion secondary to decreased atrial stretch, the observed hemodynamic actions were not mediated by an indirect increase in ANP.

Administration of DNP in mild and overt CHF uniquely increased GFR, an action not observed in normals. In the absence of an increase in renal blood flow, the glomerular actions of DNP may be explained by afferent arteriolar dilatation and efferent arteriolar constriction and/or a direct action to increase the coefficient for filtration. This increase in GFR is significant as it occurred during a further reduction in renal perfusion pressure. The high dose DNP was significantly natriuretic in all groups. Although the natriuretic action of DNP was attenuated in overt CHF, the increase in sodium excretion occurred despite significant reductions in mean arterial pressure. In addition, the natriuretic action was associated with a decrease in proximal reabsorption of sodium as determined by the lithium clearance technique. This renal response, particularly in GFR, is important as a characteristic of overt experimental CHF is a renal hyporesponsiveness to exogenously administered ANP (Cavero et al., 1990). High dose DNP also resulted in a significant diuretic response in all groups. Thus, the renal actions of DNP appear to be unique in as much as despite further reductions in renal perfusion pressure, GFR increased and proximal reabsorption of sodium decreased in association with both natriuresis and diuresis.

DNP-LI in normal human plasma averages 6 pg/ml with a range from 2 to 11 pg/ml. In human CHF (NYHA III or IV), plasma DNP-LI averages 37 pg/ml with a range from 3 to 200 pg/ml. Using a specific and sensitive radioimmunoassay, normal canine plasma DNP-LI averages 6 pg/ml with a range from 4 to 7 pg/ml. In canine experimental CHF plasma DNP-LI is increased to an average of 12 pg/ml and with a range from 9 to 15 pg/ml. The plasma concentrations of DNP in CHF are less than those reported for ANP and BNP but above those reported for CNP (Burnett et al., 1986; Wei et al., 1993).

Two different doses for DNP administration were chosen to establish a broad range of plasma concentrations to define potential therapeutic actions of DNP in CHF. Importantly, the lower dose of 10 ng/kg/minute DNP achieved circulating concentrations of approximately 300 pg/ml in normals and CHF groups, which are near the upper range of those observed in human heart failure and thus may be considered pathophysiologic. The higher dose, 50 ng/kg/minute, clearly establishes the pharmacologic actions of DNP. Using this dose, plasma concentrations of DNP achieved approximately 3,000 pg/ml in normals, but only 1,000 pg/ml in both CHF groups. The reduced plasma levels of DNP achieved during infusion in CHF may suggest that the half-life of infused DNP is reduced, which could reflect altered clearance mechanisms. Despite the lower levels of DNP achieved in CMF during the infusion, the tissue responsiveness to DNP is preserved and possibly enhanced as suggested by the increase in the plasma cGMP to plasma DNP ratio (FIG. 12).

ANP has been reported to be renin-inhibiting in normals as well as in human CHF, while the inhibitory effects in heart failure are attenuated (Richards et al., 1988; Nicholls, 1994). DNP shares this action as the ability of low dose DNP to decrease PRA was observed in normals and also in overt CHF. In contrast, this action is not seen during short-term administration of exogenous BNP in normal and CHF dogs in which BNP does not suppress PRA (Clavell et al., 1993). Such renin inhibitory actions occurred despite the presence of known renin-stimuli such as reductions in atrial pressure and renal perfusion pressure.

The therapeutic potential of the exogenous administration of DNP is further supported by the report of a clinical trial in CHF in which preserving renal function, particularly glomerular filtration rate, was the most important determinant of survival in patients with severe CHF (Girbes et al., 1998). Further, this GFR enhancing action was associated with the ability of DNP to decrease markedly elevated cardiac filling pressures in association with natriuresis, diuresis and renin inhibitory properties. These actions were further associated with a preserved ability for DNP to activate the cGMP second messenger system.

REFERENCES

Abdallah et al., *Biol. Cell*, 85, 1 (1995).
Adelman et al., *DNA*, 2, 183 (1983).
Almquist et al., *J. Med. Chem.*, 23, 1392 (1980) (—$COCH_2$—).
Atlas et al., in *Atrial Hormones and Other Natriuretic Factors*, P. J. Mulrow et al., edS., Am. Physiol. Soc., Bethesda, Md., pp. 53-76 (1987).
Barany and Merrifield, in *The Peptides*, E. Gross and F. Meinenhofer, eds., Vol. 2, Academic Press, pp. 3-285 (1980).
Baumgartner et al., *Circulation*, 96, 1 (1997).
Brenner et al., *Physiol. Rev.*, 70, 665 (1990).
Bruneau et al., *Am. J. Physiol.*, 273, H2678 (1997).
Burnett et al., *Science*, 231, 1145 (1986).
Burnett et al., *Am. J. Physiol.*, 247, F863 (1984).
Cavero et al., *Circul.*, 82, 196 (1990).
Carpino et al., *J. Org. Chem.*, 37, 3404 (1972).
Clavell et al., *Am. J. Physiol.*, 265, R1416 (1993).
Crea et al., *Proc. Natl. Acad. Sci. U.S.A.*, 75, 5765 (1978).
Dayhoff, in *Atlas of Protein Sequence and Structure*, volume 5, National Biomedical Research Foundation, pp. 101-110 (1972), and Supplement 2 to this volume, pp. 1-10.
de Bold et al., *Life Sci.*, 28, 89 (1981).
Donnelly et al., *Ann. N.Y. Acad. Sci.*, 772, 40 (1995).
Edwards et al., *Circ. Res.*, 62, 191 (1988).
Flynn et al., *Biochem. Biophys. Res. Commun.*, 117, 859 (1981).
Girbes et al., *J. Am. Coll. Cardial.*, 31, 154A (1998).
Goeddel et al., *Nucleic Acids Res.*, 8, 4057 (1980).
Grantham et al., in *Natriuretic Peptides in Health and Disease*, Samson W. K., Levin E. R., eds, J; Humana Press, pp. 309-326 (1997).
Hann, *J. Chem. Soc. Perkin Trans.*, I, 307 (1982).
Holladay et al., *Tetrahedron Lett.*, 24, 4401 (1983).
Hruby, *Life Sci.*, 31, 189 (1982).
Hudson et al., *Int. J. Pept. Prot. Res.*, 14, 177 (1979).
Jennings-White et al., *Tetrahedron Lett.*, 23, 2533 (1982).
Kambayashi et al., *FEBS Lett.*, 259, 341 (1990).
Koller et al., *Science*, 252, 120 (1991).
Lawn et al., *Nucleic Acids Res.*, 9, 6103 (1981).
Lebl and V. J. Hruby *Tetrahedron Lett.*, 25, 2067 (1984).
Lin et al., *Hypertension*, 26, 847 (1990).
Lisy et al., *J. Am. Coll. Cardiol.*, 33, 1199 (1999a).
Lisy et al., *Circl.*, 100, I-636 (1999a).
Lisy et al., *Kid. Int.*, 56, 502 (1999b).
McDonagh et al., *Lancet*, 351, 9 (1998).
Meienhofer, in *Hormonal Proteins and Peptides*, C. H. Li, ed., Vol. 2 Academic Press, pp. 48-267 (1973).
Meinhofer, *Int. J. Pept. Pro. Res.*, 11, 246 (1978).
Merrifield, *J. Am. Chem. Soc.*, 85, 2149 (1963).
Molling, *J. Mol. Med.*, 75, 242 (1997).
Morley, *Trends Pharm. Sci. pp.* 463-468 (1980).
Mukoyama et al., *J. Clin. Invest.*, 87, 1402 (1991).
Mullis et al., *Cold Spring Harbor Symp. Quant. Biol.*, 51, 263 (1987); Erlich, ed., PCR Technology, (Stockton Press, NY, 1989).
Needleman and Wunsch, *J. Mol. Biol.*, 48, 443 (1970).
Nicholls, *J. Int. Med.*, 235, 515 (1999).
Pardoll et al., *Immunity*, 3, 165 (1995).
Pearson and Lipman, *Proc. Natl. Acad. Sci.* (U.S.A.), 85, 2444 (1988).
Redfield et al., *Circ.*, 87, 2016 (1993).
Richards et al., *J. Clin. Endo. Metab.*, 67, 1134 (1988).
Sambrook et al., *Molecular Cloning: A Laboratory Manual*, Cold Spring Habor Laboratory Press, N.Y. (1989)
Schiller et al., *Biochem. Biophy. Res. Comm.*, 127, 558 (1985).
Schiller et al., *Int. J. Peptide and Protein Res.*, 25, 171 (1985).

Schirger et al., *Mayo Clin. Proc.*, 74, 126 (1999).
Schweitz et al., *J. Biol. Chem.*, 267, 13928 (1992).
Smith and Waterman, *Adv. Appl. Math.*, 2, 482 (1981).
Spatola et al., *Life Sci.*, 38, 1243 (1986).
Spatola, *Vega Data*, Vol. 1, Issue 3 (1983).
Spatola, in *Chemistry and Biochemistry of Amino Acid Peptides and Proteins*, B. Weinstein, eds., Marcel Dekker, New York, p. 267 (1983).
Steiner et al., *J. Hypertension*, 5 (1987).
Steiner et al., *J. Biochem. Chem.*, 247, 1106 (1972).
Stevens et al., in *Pathophysiology of Tachycardia-Induced Heart Failure*, Futura Publishing Co., Inc. NY, pp. 133-151 (1996).
Stevens et al., *J. Clin. Invest.*, 95, 1101 (1995).
Stevenson et al., *Immunol. Rev.*, 145, 211 (1995).
Stewart et al., *Solid Phase Peptide Synthesis*, W. H. Freeman Co., San Francisco (1969).
Stingo et al., *Am. J. Physiol.*, 263, H1318 (1992).
Stingo et al., *Am. J. Physiol.*, 262, H308 (1992).
Sudeh et al., *Biochem. Biophys. Res. Commun.*, 168, 863 (1990).
Sudeh et al., *Nature*, 332, 78 (1988).
Suga et al., *J. Clin. Invest.*, 90, 1145 (1992).
Tawaragi et al., *Biochem. Biophys. Res. Commun.*, 175, 645 (1991).
Tripathy et al., *PNAS*, 93, 10876 (1996a).
Tripathy et al., *Nature Med.*, 2, 545 (1996b).
Tripathy et al., *PNAS*, 91 11557 (1994).
Tsurumi et al., *Circ.* 94, 3281 (1996).
Viera et al., *Meth. Enzymol.*, 153, 3 (1987).
Wei et al., *Circulation*, 88, 1004 (1993).
Wennberg et al., *Am. Coll. Cardiol.*, 29, 305A (1997).
Wolff et al., *Science*, 247, 1465 (1990).
Yamamoto et al., *Am. J. Physiol.*, 273, H2406 (1997).
Yamamoto et al., *Am. J. Physiol.*, 271, R1529 (1996).
Yang et al., *Mol. Med. Today*, 2, 476 (1996).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. A compound comprising the sequence of amino acids 24-34 of SEQ ID NO:10, wherein the compound has a biological activity selected from the group consisting of vasodilation, natriuresis, diuresis, and renin suppression, and wherein the compound does not comprise the sequence Glu-Val-Lys-Tyr-Asp-Pro-Cys-Phe-Gly-His-Lys-Ile-Asp-Arg-Ile-Asn-His-Val-Ser-Asn-Leu-Gly-Cys (SEQ ID NO:11).

2. The compound of claim 1, further comprising an amino acid sequence from the N-terminus of brain natriuretic peptide (BNP).

3. The compound of claim 2, wherein the amino acid sequence from the N-terminus of BNP is SEQ ID NO:7.

4. The compound of claim 1, further comprising an amino acid sequence from the N-terminus of C-type natriuretic peptide (CNP).

5. The compound of claim 4, wherein the amino acid sequence from the N-terminus of CNP is SEQ ID NO:8.

6. A composition useful as a natriuretic, diuretic, renin-suppressor or vasodilator comprising a therapeutically effective amount of the compound of claim 1 with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,964,564 B2 | Page 1 of 1 |
| APPLICATION NO. | : 12/120842 | |
| DATED | : June 21, 2011 | |
| INVENTOR(S) | : Burnett, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 78 days.

Signed and Sealed this
Twenty-second Day of November, 2011

David J. Kappos
*Director of the United States Patent and Trademark Office*

SEQUENCE LISTING

```
<160> NUMBER OF SEQ ID NOS: 14

<210> SEQ ID NO 1
<211> LENGTH: 41
<212> TYPE: PRT
<213> ORGANISM: Artificial Sequence
<220> FEATURE:
<223> OTHER INFORMATION: Synthetic peptide

<400> SEQUENCE: 1

Ser Pro Lys Met Val Gln Gly Ser Gly Cys Phe Gly Arg Lys Met Asp
1               5                   10                  15

Arg Ile Ser Ser Ser Ser Gly Leu Gly Cys Pro Ser Leu Arg Asp Pro
            20                  25                  30

Arg Pro Asn Ala Pro Ser Thr Ser Ala
        35                  40

<210> SEQ ID NO 2
<211> LENGTH: 37
<212> TYPE: PRT
<213> ORGANISM: Artificial Sequence
<220> FEATURE:
<223> OTHER INFORMATION: Synthetic peptide

<400> SEQUENCE: 2

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 3
<211> LENGTH: 15
<212> TYPE: PRT
<213> ORGANISM: Dendroaspis angusticeps

<400> SEQUENCE: 3

Pro Ser Leu Arg Asp Pro Arg Pro Asn Ala Pro Ser Thr Ser Ala
```

<210> SEQ ID NO 4
<211> LENGTH: 50
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: 1-35
<223> OTHER INFORMATION: Xaa is absent or any amino acid
<221> NAME/KEY: VARIANT
<222> LOCATION: 37, 47-49
<223> OTHER INFORMATION: Xaa is Ser or Thr
<221> NAME/KEY: VARIANT
<222> LOCATION: 38, 45
<223> OTHER INFORMATION: Xaa is Gly, Ala, Val, Met, Leu, Nle, or Ile
<221> NAME/KEY: VARIANT
<222> LOCATION: 39, 42, 44
<223> OTHER INFORMATION: Xaa is Leu, Lys, Arg, His, Orn, Asn, or Gln
<221> NAME/KEY: VARIANT
<222> LOCATION: 40
<223> OTHER INFORMATION: Xaa is Asp or Glu
<221> NAME/KEY: VARIANT
<222> LOCATION: 50
<223> OTHER INFORMATION: Xaa is Lys, Arg, Orn, Ala, Thr, Asn, or Gln

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Pro Xaa Xaa Xaa Xaa Pro Xaa Pro Xaa Xaa Pro Xaa Xaa
        35                  40                  45

Xaa Xaa
    50

<210> SEQ ID NO 5
<211> LENGTH: 28
<212> TYPE: PRT
<213> ORGANISM: Homo sapiens

<400> SEQUENCE: 5

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 6
<211> LENGTH: 32
<212> TYPE: PRT
<213> ORGANISM: Homo sapiens

<400> SEQUENCE: 6

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 7
<211> LENGTH: 26
<212> TYPE: PRT
<213> ORGANISM: Homo sapiens

<400> SEQUENCE: 7

Ser Pro Lys Met Val Gln Glu Ser Gly Cys Phe Gly Arg Lys Met Asp
1               5                   10                  15

```
Arg Ile Ser Ser Ser Ser Gly Leu Gly Cys
            20                  25

<210> SEQ ID NO 8
<211> LENGTH: 22
<212> TYPE: PRT
<213> ORGANISM: Homo sapiens

<400> SEQUENCE: 8

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 9
<211> LENGTH: 22
<212> TYPE: PRT
<213> ORGANISM: Homo sapiens

<400> SEQUENCE: 9

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 10
<211> LENGTH: 38
<212> TYPE: PRT
<213> ORGANISM: Dendroaspis angusticeps

<400> SEQUENCE: 10

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35

<210> SEQ ID NO 11
<211> LENGTH: 23
<212> TYPE: PRT
<213> ORGANISM: Dendroaspis angusticeps

<400> SEQUENCE: 11

Glu Val Lys Tyr Asp Pro Cys Phe Gly His Lys Ile Asp Arg Ile Asn
1               5                   10                  15

His Val Ser Asn Leu Gly Cys
            20

<210> SEQ ID NO 12
<211> LENGTH: 85
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: 1-35
<223> OTHER INFORMATION: Xaa is absent or any amino acid
<221> NAME/KEY: VARIANT
<222> LOCATION: 37, 47-49
<223> OTHER INFORMATION: Xaa is Ser or Thr
<221> NAME/KEY: VARIANT
<222> LOCATION: 38, 45
<223> OTHER INFORMATION: Xaa is Gly, Ala, Val, Met, Leu, Nle, or Ile
<221> NAME/KEY: VARIANT
```

```
<222> LOCATION: 39, 42, 44
<223> OTHER INFORMATION: Xaa is Leu, Lys, Arg, His, Orn, Asn, or Gln
<221> NAME/KEY: VARIANT
<222> LOCATION: 40
<223> OTHER INFORMATION: Xaa is Asp or Glu
<221> NAME/KEY: VARIANT
<222> LOCATION: 50
<223> OTHER INFORMATION: Xaa is Lys, Arg, Orn, Ala, Thr, Asn, or Gln
<221> NAME/KEY: VARIANT
<222> LOCATION: 51-85
<223> OTHER INFORMATION: Xaa is absent or any amino acid

<400> SEQUENCE: 12

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Pro Xaa Xaa Xaa Xaa Pro Xaa Pro Xaa Xaa Pro Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
                85

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: 2, 12-14
<223> OTHER INFORMATION: Xaa is Ser or Thr
<221> NAME/KEY: VARIANT
<222> LOCATION: 3,10
<223> OTHER INFORMATION: Xaa is Gly, Ala, Val, Met, Leu, Nle, or Ile
<221> NAME/KEY: VARIANT
<222> LOCATION: 4,7,9
<223> OTHER INFORMATION: Xaa is Leu, Lys, Arg, His, Orn, Asn, or Gln
<221> NAME/KEY: VARIANT
<222> LOCATION: 5
<223> OTHER INFORMATION: Xaa is Asp or Glu
<221> NAME/KEY: VARIANT
<222> LOCATION: 15
<223> OTHER INFORMATION: Xaa is Lys, Arg, Orn, Ala, Thr, Asn, or Gln

<400> SEQUENCE: 13

Pro Xaa Xaa Xaa Xaa Pro Xaa Pro Xaa Xaa Pro Xaa Xaa Xaa Xaa
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: 2
<223> OTHER INFORMATION: Xaa is Ser or Thr
<221> NAME/KEY: VARIANT
<222> LOCATION: 3, 10
<223> OTHER INFORMATION: Xaa is Gly, Ala, Val, Met, Leu, Nle or Ile
<221> NAME/KEY: VARIANT
<222> LOCATION: 4, 7, 9
<223> OTHER INFORMATION: Xaa is Leu, Lys, Arg, His, Orn, Asn or Gln
<221> NAME/KEY: VARIANT
<222> LOCATION: 5
<223> OTHER INFORMATION: Xaa is Asp or Glu
```

```
<400> SEQUENCE: 14

Pro Xaa Xaa Xaa Xaa Pro Xaa Pro Xaa Xaa Pro
1               5                   10
```